US012391984B2

(12) United States Patent
Dockter

(10) Patent No.: US 12,391,984 B2
(45) Date of Patent: Aug. 19, 2025

(54) COMPOSITIONS AND METHODS FOR ROLLING CIRCLE AMPLIFICATION

(71) Applicant: 10x Genomics, Inc., Pleasanton, CA (US)

(72) Inventor: Rhyan Blaine Dockter, Logan, UT (US)

(\*) Notice: Subject to any disclaimer, the term of this patent is extended or adjusted under 35 U.S.C. 154(b) by 0 days.

(21) Appl. No.: 17/816,985

(22) Filed: Aug. 2, 2022

(65) Prior Publication Data

US 2023/0044650 A1 Feb. 9, 2023

Related U.S. Application Data

(60) Provisional application No. 63/228,802, filed on Aug. 3, 2021.

(51) Int. Cl.
*C12Q 1/6853* (2018.01)
*C12Q 1/6841* (2018.01)

(52) U.S. Cl.
CPC ......... *C12Q 1/6853* (2013.01); *C12Q 1/6841* (2013.01)

(58) Field of Classification Search
CPC .. C12Q 1/6853; C12Q 1/6841; C12Q 1/6844; C12Q 2525/301; C12Q 2531/125
See application file for complete search history.

(56) References Cited

U.S. PATENT DOCUMENTS

| | | | |
|---|---|---|---|
| 4,318,846 A | 3/1982 | Khanna et al. |
| 4,757,141 A | 7/1988 | Fung et al. |
| 4,849,336 A | 7/1989 | Miyoshi et al. |
| 5,066,580 A | 11/1991 | Lee |
| 5,091,519 A | 2/1992 | Cruickshank |
| 5,151,507 A | 9/1992 | Hobbs et al. |
| 5,188,934 A | 2/1993 | Menchen |
| 5,198,537 A | 3/1993 | Huber et al. |
| 5,344,757 A | 9/1994 | Holtke et al. |
| 5,354,657 A | 10/1994 | Boehringer et al. |
| 5,366,860 A | 11/1994 | Bergot et al. |
| 5,599,675 A | 2/1997 | Brenner |
| 5,635,352 A | 6/1997 | Urdea et al. |
| 5,688,648 A | 11/1997 | Mathies |
| 5,695,940 A | 12/1997 | Drmanac et al. |
| 5,702,888 A | 12/1997 | Holtke et al. |
| 5,750,341 A | 5/1998 | Macevicz |
| 5,800,996 A | 9/1998 | Lee et al. |
| 5,847,162 A | 12/1998 | Lee et al. |
| 5,990,479 A | 11/1999 | Weiss et al. |
| 6,054,274 A | 4/2000 | Sampson et al. |
| 6,172,218 B1 | 1/2001 | Brenner |
| 6,207,392 B1 | 3/2001 | Weiss et al. |
| 6,251,303 B1 | 6/2001 | Bawendi et al. |
| 6,265,552 B1 | 7/2001 | Schatz |
| 6,291,187 B1 | 9/2001 | Kingsmore et al. |
| 6,306,597 B1 | 10/2001 | Macevicz |
| 6,319,426 B1 | 11/2001 | Bawendi et al. |
| 6,322,901 B1 | 11/2001 | Bawendi et al. |
| 6,323,009 B1 | 11/2001 | Lasken et al. |
| 6,344,329 B1 | 2/2002 | Lizardi et al. |
| 6,368,801 B1 | 4/2002 | Faruqi |
| 6,391,937 B1 | 5/2002 | Beuhler et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,534,266 B1 | 3/2003 | Singer |
| 6,576,291 B2 | 6/2003 | Bawendi et al. |
| 6,969,488 B2 | 11/2005 | Bridgham et al. |
| 7,057,026 B2 | 6/2006 | Barnes et al. |
| 7,255,994 B2 | 8/2007 | Lao |
| 7,264,929 B2 | 9/2007 | Rothberg et al. |
| 7,473,767 B2 | 1/2009 | Dimitrov |
| 7,534,991 B2 | 5/2009 | Miller et al. |
| 7,555,155 B2 | 6/2009 | Levenson et al. |
| 7,632,641 B2 | 12/2009 | Dirks et al. |
| 7,655,898 B2 | 2/2010 | Miller |
| 7,721,721 B1 | 5/2010 | Kronengold et al. |
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |

(Continued)

FOREIGN PATENT DOCUMENTS

WO WO 1991/017160 11/1991
WO WO 2014/163886 10/2014

(Continued)

OTHER PUBLICATIONS

Zanoli (Biosensors 2013, 3, 18-43).*
Du (Chem. Commun., 2016,52, 1272.).*
Chen (Analyst, 2017, 142, 3048).*
Niimitphak (MolecularandCellularProbes24(2010)1-5).*
Nagmine (Molecular and Cellular Probes (2002) 16, 223-229).*
Conze (Nucleic Acids Research, 2010, vol. 38, No. 16 e163).*
Yang (Anal. Chem. 2007, 79, 3320-3329).*
Deng (Chem4,1373-1386,Jun. 14, 2018).*
Liu (Nanoscale, 2019, 11, 17179).*
Liu (J. Mater. Chem. B, 2018,6, 4638).*
Dirks et al., "Triggered amplification by hybridization chain reaction," Proc Natl Acad Sci U S A. (2004) 101(43): 15275-15278.
Allawi et al., "Thermodynamics and NMR of internal G.T mismatches in DNA," Biochemistry, (1997) 36:10581-94.

(Continued)

*Primary Examiner* — Steven Pohnert
(74) *Attorney, Agent, or Firm* — MORRISON & FOERSTER LLP

(57) ABSTRACT

The present disclosure in some aspects relates to methods and compositions for accurately detecting and quantifying multiple analytes present in a biological sample. In some aspects, the methods and compositions provided herein address one or more issues associated with the stability and/or size of nucleic acid structures such as rolling circle amplification products in the biological sample.

10 Claims, 6 Drawing Sheets

Specification includes a Sequence Listing.

(56) References Cited

U.S. PATENT DOCUMENTS

| | | |
|---|---|---|
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,658,361 B2 | 2/2014 | Wu et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,217,178 B2 | 12/2015 | Fedurco et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,512,422 B2 | 12/2016 | Barnard et al. |
| 9,541,504 B2 | 1/2017 | Hoyt |
| 9,551,032 B2 | 1/2017 | Landegren et al. |
| 9,624,538 B2 | 4/2017 | Church et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,889,422 B2 | 2/2018 | Smith et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,550,429 B2 | 2/2020 | Harada et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,459,603 B2 | 10/2022 | Tyagi et al. |
| 2002/0045045 A1 | 4/2002 | Adams et al. |
| 2003/0013091 A1 | 1/2003 | Dimitrov |
| 2003/0017264 A1 | 1/2003 | Treadway et al. |
| 2005/0100900 A1 | 5/2005 | Kawashima et al. |
| 2006/0188901 A1 | 8/2006 | Barnes et al. |
| 2006/0234261 A1 | 10/2006 | Pierce et al. |
| 2006/0240439 A1 | 10/2006 | Smith et al. |
| 2006/0281109 A1 | 12/2006 | Barr et al. |
| 2007/0166705 A1 | 7/2007 | Milton et al. |
| 2007/0166708 A1 | 7/2007 | Dimitrov et al. |
| 2009/0118128 A1 | 5/2009 | Liu et al. |
| 2010/0015607 A1 | 1/2010 | Geiss et al. |
| 2010/0047924 A1 | 2/2010 | Webster et al. |
| 2010/0055733 A1 | 3/2010 | Lutolf et al. |
| 2010/0112710 A1 | 5/2010 | Geiss et al. |
| 2010/0261026 A1 | 10/2010 | Ferree et al. |
| 2010/0262374 A1 | 10/2010 | Hwang et al. |
| 2011/0059865 A1 | 3/2011 | Smith et al. |
| 2011/0223585 A1 | 9/2011 | Gullberg et al. |
| 2012/0270305 A1 | 10/2012 | Reed et al. |
| 2013/0079232 A1 | 3/2013 | Kain et al. |
| 2013/0260372 A1 | 10/2013 | Buermann et al. |
| 2013/0288249 A1 | 10/2013 | Gullbert |
| 2013/0323729 A1 | 12/2013 | Landegren et al. |
| 2014/0194311 A1 | 7/2014 | Gullberg et al. |
| 2014/0371088 A1 | 12/2014 | Webster |
| 2016/0024555 A1 | 1/2016 | Church et al. |
| 2016/0108458 A1 | 4/2016 | Frei et al. |
| 2016/0305856 A1 | 10/2016 | Boyden et al. |
| 2016/0369329 A1 | 12/2016 | Cai et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0219465 A1 | 8/2017 | Desseroth et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0251833 A1 | 9/2018 | Daugharthy et al. |
| 2018/0320226 A1 | 11/2018 | Church et al. |
| 2019/0017106 A1 | 1/2019 | Frisen et al. |
| 2019/0032121 A1 | 1/2019 | Daugharthy et al. |
| 2019/0032128 A1 | 1/2019 | Chen et al. |
| 2019/0055594 A1 | 2/2019 | Samusik et al. |
| 2019/0106733 A1 | 4/2019 | Kishi et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0177800 A1 | 6/2019 | Boutet et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2019/0367969 A1 | 12/2019 | Belhocine |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2020/0399689 A1 | 12/2020 | Luo et al. |
| 2021/0017587 A1 | 1/2021 | Cai et al. |
| 2021/0115504 A1 | 4/2021 | Cai et al. |
| 2021/0198723 A1 | 7/2021 | Kuhnemund et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340618 A1 | 11/2021 | Kuhnemund et al. |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0010358 A1 | 1/2022 | Kuhnemund et al. |
| 2022/0049302 A1 | 2/2022 | Daugharthy et al. |
| 2022/0049303 A1 | 2/2022 | Busby et al. |

(56) References Cited

U.S. PATENT DOCUMENTS

| | | |
|---|---|---|
| 2022/0064697 A1 | 3/2022 | Zhuang et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |

FOREIGN PATENT DOCUMENTS

| | | |
|---|---|---|
| WO | WO 2017/079406 | 5/2017 |
| WO | WO 2017/143155 | 8/2017 |
| WO | WO 2018/026873 | 2/2018 |
| WO | WO 2018/089438 | 5/2018 |
| WO | WO 2019/199579 | 10/2019 |
| WO | WO 2020/076976 | 4/2020 |
| WO | WO 2020/076979 | 4/2020 |
| WO | WO 2020/096687 | 5/2020 |
| WO | WO 2020/099640 | 5/2020 |
| WO | WO 2020/117914 | 6/2020 |
| WO | WO 2020/123316 | 6/2020 |
| WO | WO 2020/123742 | 6/2020 |
| WO | WO 2020/142490 | 7/2020 |
| WO | WO 2020/240025 | 12/2020 |
| WO | WO 2020/254519 | 12/2020 |
| WO | WO 2021/123282 | 6/2021 |
| WO | WO 2021/123286 | 6/2021 |
| WO | WO 2021/138676 | 7/2021 |
| WO | WO 2021/155063 | 8/2021 |
| WO | WO 2021/168326 | 8/2021 |

OTHER PUBLICATIONS

Archer et al., "Selective and flexible depletion of problematic sequences from RNA-seq libraries at the cDNA stage," BMC Genomics. (2014) 15(1):401.

Baner et al., "Signal amplification of padlock probes by rolling circle replication," Nucleic Acids Res. (1998) 26(22):5073-5078.

Bibikova et al., "Quantitative gene expression profiling in formalin-fixed, paraffin-embedded tissues using universal bead arrays," Am J Pathol. Nov. 2004;165(5):1799-807.

Bolognesi et al., "Multiplex Staining by Sequential Immunostaining and Antibody Removal on Routine Tissue Sections," J. Histochem. Cytochem. (2017); 65(8): 431-444.

Capodieci et al., "Gene expression profiling in single cells within tissue," Nat Methods. (2005) 2(9): 663-5.

Chemeris et al., "Real-time hybridization chain reaction," Dokl Biochem Biophys. (2008) 419: 53-55.

Chen et al., "Nanoscale imaging of RNA with expansion microscopy," Nat Methods. (2016) 13:679-684.

Chen et al., "RNA imaging. Spatially resolved, highly multiplexed RNA profiling in single cells," Science. (2015) 348(6233): aaa6090. 16 pgs.

Chen et al., "Expansion Microscopy," Science (2015) 347(6221):543-548.

Choi et al., "Programmable in situ amplification for multiplexed imaging of mRNA expression," Nat Biotechnol. (2010) 28(11): 1208-1212.

Clausson et al., "Compaction of rolling circle amplification products increases signal integrity and signal-to-noise ratio," Sci Rep. (2015) 5:12317.

Conze et al., "Single molecule analysis of combinatorial splicing," Nucleic Acids Res. (2010) 38(16): e163.

Dean et al., "Rapid Amplification of Plasmid and Phage DNA Using Phi29 DNA Polymerase and Multiply-Primed Rolling Circle Amplification," Genome Research (2001) 11:1095-1099.

Eng et al., "Transcriptome-scale super-resolved imaging in tissues by RNA seqFISH," Nature. (2019) 568(7751): 235-239.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Faruqi et al., "High-throughput genotyping of single nucleotide polymorphisms with rolling circle amplification," BMC Genomics. (2001) 2:4.

Femino et al., "Visualization of single RNA transcripts in situ," Science. (1998) 280(5363): 585-90.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Glass et al., "SIMPLE: a sequential immunoperoxidase labeling and erasing method," J Histochem Cytochem. (2009) 57(10); 899-905.

Goh, J.J.L. et al. (Jul. 2020, e-pub. Jun. 15, 2020). "Highly Specific Multiplexed RNA Imaging in Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Gunderson et al. "Decoding randomly ordered DNA arrays." Genome research 14.5 (2004): 870-877.

Gyllborg et al., "Hybridization-based in situ sequencing (HybISS) for spatially resolved transcriptomics in human and mouse brain tissue," Nucleic Acids Res. (2020) 48(19): e112.

Han et al., "Quantum-dot-tagged microbeads for multiplexed optical coding of biomolecules," Nat Biotechnol. (2001) 19(7): 631-5.

Henegariu et al., "Custom fluorescent-nucleotide synthesis as an alternative method for nucleic acid labeling," Nature Biotechnol. (2000) 18:345.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Jamur et al., "Permeabilization of cell membranes," Method Mol. Biol. (2010) 588: 63-66 (abstract only).

Kanehisa, "Use of statistical criteria for screening potential homologies in nucleic acid sequences," Nucleic Acids Res. (1984) 12:203-213.

Korlach et al. "Selective aluminum passivation for targeted immobilization of single DNA polymerase molecules in zero-mode waveguide nanostructures." Proceedings of the National Academy of Sciences 105.4 (2008): 1176-1181.

Lagunavicius et al., "Novel application of Phi29 DNA polymerase: RNA detection and analysis in vitro and in situ by target RNA-primed RCA," RNA. (2009) 15(5):765-71.

Lakowicz et al., "Silver particles enhance emission of fluorescent DNA oligomers," Bio Techniques (2003) 34(1); 62-66.

Larsson et al. "In situ detection and genotyping of individual mRNA molecules," Nat Methods. (2010) 7(5):395-397.

Lee et al. "Highly Multiplexed Subcellular RNA Sequencing In Situ", Science (2014) 343(6177):1360-1363.

Levene et al. "Zero-mode waveguides for single-molecule analysis at high concentrations." science 299.5607 (2003): 682-686.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Lin et al., "Highly multiplexed imaging of single cells using a high-throughput cyclic immunofluorescence method," Nat Commun. (2015) 6:8390.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

Lizardi et al., "Mutation detection and single-molecule counting using isothermal rolling-circle amplification," Nat Genet. (1998) 19(3): 225-232.

Lundquist et al. "Parallel confocal detection of single molecules in real time." Optics letters 33.9 (2008): 1026-1028.

(56) References Cited

OTHER PUBLICATIONS

Lyamichev et al., "Comparison of the 5' nuclease activities of taq DNA polymerase and its isolated nuclease domain," Proc Natl Acad Sci USA. (1999) 96(11): 6143-6148.

Ma et al., "RNA template-dependent 5' nuclease activity of Thermus aquaticus and Thermus thermophilus DNA polymerases," J Biol Chem. (2000) 275(32): 24693-700.

Maierhorfer et al., "Multicolor deconvolution microscopy of thick biological specimens," Am J Pathol. (2003) 162(2): 373-9.

McGinn et al., "New technologies for DNA analysis—a review of the READNA Project," N Biotechnol. (2016) 33(3): 311-30. doi: 10.1016/j.nbt.2015.10.003.

Meade et al. "Multiplexed DNA detection using spectrally encoded porous SiO2 photonic crystal particles," Anal Chem. (2009) 81(7): 2618-25.

Mitra et al., "Fluorescent in situ sequencing on polymerase colonies," Anal. Biochem. (2003) 320, 55-65.

Moffitt et al., "RNA Imaging with Multiplexed Error-Robust Fluorescence In Situ Hybridization (MERFISH)," Methods in Enzymology, (2016) 572; 1-49.

Mohsen et al., "The Discovery of Rolling Circle Amplification and Rolling Circle Transcription," Acc Chem Res. (2016) 49(11): 2540-2550.

Nallur et al., "Signal amplification by rolling circle amplification on DNA microarrays," Nucleic Acids Res. (2001) 29(23): e118.

Niu et al., "Fluorescence detection for DNA using hybridization chain reaction with enzyme-amplification," Chem Commun (Camb). (2010) 46(18): 3089-91.

Payne et al. "In situ genome sequencing resolves DNA sequence and structure in intact biological samples," Science. (2021) 371(6532): eaay3446. doi: 10.1126/science.aay3446. Epub Dec. 31, 2020.

Pirici et al., "Antibody elution method for multiple immunohistochemistry on primary antibodies raised in the same species and of the same subtype," J Histochem Cytochem. (2009) 57(6); 567-75.

Raj et al., "Imaging individual mRNA molecules using multiple singly labeled probes," Nat Methods. (2008) 5(10): 877-879.

Rouhanifard et al. "ClampFISH detects individual nucleic acid molecules using click chemistry-based amplification," Nat Biotechnol. (2018) 17 pages. doi: 10.1038/nbt.4286.

Schweitzer et al. "Immunoassays with rolling circle DNA amplification: A versatile platform for ultrasensitive antigen detection," Proc. Natl Acad. Sci. USA (2000) 97:10113-119.

Schweitzer et al., "Multiplexed protein profiling on microarrays by rolling-circle amplification," Nature Biotech. (2002) 20:359-365.

Shendure et al, "Accurate multiplex polony sequencing of an evolved bacterial genome," Science (2005) 309(5741); 1728-1732.

Song et al., "Hybridization chain reaction-based aptameric system for the highly selective and sensitive detection of protein," Analyst. (2012) 137(6):1396-1401.

Sun et al., "Composite organic-inorganic nanoparticles as Raman labels for tissue analysis," Nano Lett. (2007) 7(2): 351-6.

Takei et al., (Feb. 2021, e-pub Jan. 27, 2021). "Integrated Spatial Genomics Reveals Global Architecture of Single Nuclei," Nature 590(7845):344-350, 53 pages. doi: 10.1038/s41586-020-03126-2.

Vandernoot et al., "cDNA normalization by hydroxyapatite chromatography to enrich transcriptome diversity in RNA-seq applications," Biotechniques, (2012) 53(6) 373-80.

Wählby et al., "Sequential immunofluorescence staining and image analysis for detection of large numbers of antigens in individual cell nuclei," Cytometry. (2002) 47(1): 32-41.

Wang et al., "Three-dimensional intact-tissue sequencing of single-cell transcriptional states," Science. (2018) 361(6400): eaat5691.

Weibrecht et al., "Simultaneous visualization of both signaling cascade activity and end-point gene expression in single cells," PLoS One. (2011) 6(5): e20148.

Wetmur, "DNA Probes: Applications of the Principles of Nucleic Acid Hybridization," Critical Reviews in Biochemistry and Molecular Biology, (1991) 26(91); 227-259.

Wilson et al., "Encoded microcarriers for high-throughput multiplexed detection," Angew Chem Int Ed Engl. (2006) 18;45(37): 6104-17.

Wu, C. et al. "RollFISH Achieves Robust Quantification of Single-Molecule RNA Biomarkers in Paraffin-Embedded Tumor Tissue Samples," Commun Biol. (2018) 1:(209):1-8. doi: 10.1038/s42003-018-0218-0.

Xia et al. "Multiplexed detection of RNA using MERFISH and branched DNA amplification." Scientific reports 9.1 (2019): 1-13.

Zhao et al., "Advances of multiplex and high throughput biomolecular detection technologies based on encoding microparticles," Sci China Chem. (2011) 54(8):1185.

\* cited by examiner

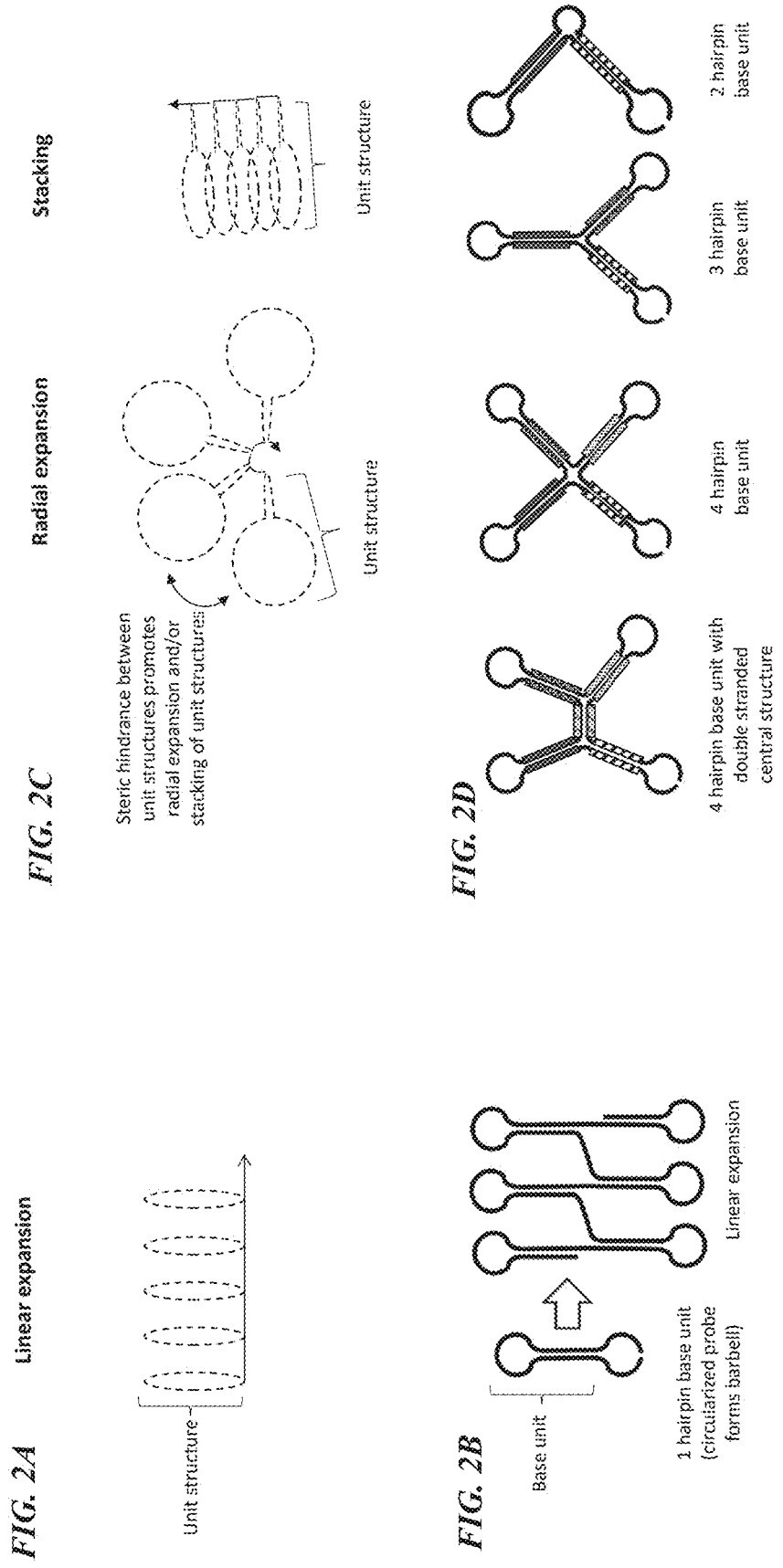

COMPOSITIONS AND METHODS FOR ROLLING CIRCLE AMPLIFICATION

CROSS-REFERENCE TO RELATED APPLICATION

This application claims priority to U.S. Provisional Patent Application No. 63/228,802, filed Aug. 3, 2021, entitled "COMPOSITIONS AND METHODS FOR ROLLING CIRCLE AMPLIFICATION," which is herein incorporated by reference in its entirety for all purposes.

REFERENCE TO AN ELECTRONIC SEQUENCE LISTING

The contents of the electronic sequence listing (202412007500SEQLIST.xml; Size: 2,827 bytes; and Date of Creation: Jul. 18, 2022) is herein incorporated by reference in its entirety.

FIELD

The present disclosure relates in some aspects to methods and compositions for analyzing a biological sample, such as for stabilizing and/or compacting nucleic acid structures in the biological sample for in situ analysis.

BACKGROUND

Methods are available for analyzing nucleic acids in a biological sample in situ, such as a cell or a tissue. For instance, advances in single molecule fluorescent hybridization (smFISH) have enabled nanoscale-resolution imaging of RNA in cells and tissues. However, oligonucleotide probe-based assay methods for in situ analysis may suffer from low sensitivity, specificity, and/or detection efficiency and may require careful and laborious optimization. Furthermore, the dynamic range of rolling circle amplification-based methods may be limited by the ability to spatially resolve individual rolling circle amplification products. Improved methods for in situ analysis are needed. The present disclosure addresses these and other needs.

BRIEF SUMMARY

There is a need for increasing the stability and/or compaction of structures comprising nucleic acid molecules (e.g., nucleic acid concatemers such as rolling circle amplification products) during in situ analysis of a biological sample. For example, probe/target hybridization complexes and/or rolling circle amplification products may become destabilized (e.g., when wash conditions are too stringent), which may result in a decrease in the number of useful signals, impaired spatial fidelity of signals between hybridization cycles, and loss of information in the assay. Furthermore, compaction of nucleic acid in the sample (e.g., a cell or tissue sample) may allow for better resolution of signals. In some examples, if a plurality of target molecules are being targeted and analyzed in a cell, detectable signals (e.g., fluorescent puncta) may become crowded and the differentiating between signals may become challenging. In some cases, compaction of nucleic acid in the sample (e.g., a cell or tissue sample) may allow for more analytes to be detected simultaneously.

Provided herein are methods and compositions for compaction and/or stabilization of structures comprising nucleic acid molecules in situ in a biological sample, including methods for enhancing the stability and/or compaction of nucleic acid molecules during in situ analysis, e.g., for decoding nucleic acid barcode sequences through sequential cycles of detectable probe hybridization (directly or indirectly) to the nucleic acid molecules (e.g., nucleic acid concatemers such as rolling circle amplification products).

In some aspects, provided herein is a method for analyzing a biological sample, comprising: (a) hybridizing a circular probe or circularizable probe or probe set to a sequence of a target nucleic acid in the biological sample, wherein the circular probe or circularizable probe or probe set comprises a first stem-loop structure, a second stem-loop structure, and a third stem-loop structure, and (b) generating an amplification product using the circular probe or a circularized probe generated from the circularizable probe or probe set as a template, wherein the amplification product comprises multiple copies of a unit structure comprising complementary sequences of the first stem-loop structure, the second stem-loop structure, and the third stem-loop structure.

In some embodiments, the circular probe or circularizable probe or probe set can comprise a double stranded central structure between the stem regions of the first and second stem-loop structures and the double stranded central structure is non-overlapping with the stem regions of the first, second, or third stem-loop structures.

In any of the embodiments herein, the circular probe or circularizable probe or probe set comprises a fourth stem-loop structure. In some embodiments, a first strand of the double stranded central structure is between the stem regions of the first and second stem-loop structures and a second strand of the double stranded central structure is between the stem regions of the third and fourth stem-loop structures.

In any of the embodiments herein, a copy of the unit structure in the amplification product can be symmetrical.

In any of the embodiments herein, the sequences that form the double stranded central structure may be non-overlapping with the sequences that form the first, second, third or fourth stem-loop structures.

In any of the embodiments herein, the method can comprise generating the circularized probe from the circularizable probe or probe set. In some embodiments, the generating can comprise ligating a 5' end sequence and a 3' end sequence of the circularizable probe or probe set.

In some embodiments, the 5' end sequence and the 3' end sequence can be in the loop region of the first, second, third, or fourth stem-loop structure. In any of the embodiments herein, the 5' end sequence and the 3' end sequence can be hybridized to the target nucleic acid. In some embodiments, the 5' end sequence and the 3' end sequence are ligated using the target nucleic acid as a template. Alternatively, In any of the embodiments herein, the 5' end sequence and the 3' end sequence can be hybridized to a splint that is distinct from the circularizable probe or probe set and the target nucleic acid, optionally wherein the 5' end sequence and the 3' end sequence are ligated using the splint as a template. In some embodiments, the splint comprises a sequence that hybridizes to the target nucleic acid.

In some embodiments, the 5' end sequence and the 3' end sequence can be in a strand of the stem region of the first, second, third, or fourth stem-loop structure. In some embodiments, the 5' end sequence and the 3' end sequence are ligated using the other strand of the stem region as a template.

In some embodiments, the 5' end sequence and the 3' end sequence can be in a strand of the double stranded central structure. In some embodiments, the 5' end sequence and the 3' end sequence are ligated using the other strand of the double stranded central structure as a template.

In any of the embodiments herein, the circularized probe can be generated from the circularizable probe set.

In any of the embodiments herein, the circularizable probe set can comprise a first nucleic acid molecule and a second nucleic acid molecule. In some embodiments, hybridization of the first nucleic acid molecule with the second nucleic acid molecule forms one or more stem regions or portion(s) thereof and/or the double stranded central structure or a portion thereof.

In any of the embodiments herein, the generating can comprise a first ligation and a second ligation. In some embodiments, the first ligation is of a 5' end of the first nucleic acid molecule to a 3' end of the second nucleic acid molecule and the second ligation is of a 3' end of the first nucleic acid molecule and a 5' end of the second nucleic acid molecule.

In some embodiments, the first ligation and the second ligation are performed using the target nucleic acid as a template for ligation. Alternatively, in some embodiments, the first ligation is performed using the target nucleic acid as a template for ligation, and the second ligation is performed using a strand of a stem region of the circularizable probe set as a template, or using a splint that is distinct from the circularizable probe or probe set and the target nucleic acid.

In any of the embodiments herein, the first nucleic acid molecule and second nucleic acid molecule can be hybridized to each other prior to hybridizing the circularizable probe set to the target nucleic acid.

In any of the embodiments herein, the circularized probe can be generated using enzymatic ligation and/or chemical ligation In any of the embodiments herein, the circularized probe can be generated using template dependent ligation and/or template independent ligation.

In any of the embodiments herein, the circularized probe can be generated using a ligase having an RNA-templated DNA ligase activity and/or an RNA-templated RNA ligase activity.

In any of the embodiments herein, the circularized probe can be generated using a ligase selected from the group consisting of a Chlorella virus DNA ligase (PBCV DNA ligase), a T4 RNA ligase, a T4 DNA ligase, and a single-stranded DNA (ssDNA) ligase.

In any of the embodiments herein, the circularized probe can be generated using a PBCV-1 DNA ligase or variant or derivative thereof and/or a T4 RNA ligase 2 (T4 Rnl2) or variant or derivative thereof.

In any of the embodiments herein, the circularized probe can be generated in situ in the biological sample or in a matrix embedding the biological sample or molecules thereof.

In any of the embodiments herein, the amplification product can be a rolling circle amplification (RCA) product. In some embodiments, the amplification product can be generated using linear RCA, branched RCA, dendritic RCA, or any combination thereof.

In any of the embodiments herein, the amplification product can be generated using a polymerase selected from the group consisting of Phi29 DNA polymerase, Phi29-like DNA polymerase, M2 DNA polymerase, B103 DNA polymerase, GA-1 DNA polymerase, phi-PRD1 polymerase, Vent DNA polymerase, Deep Vent DNA polymerase, Vent (exo-) DNA polymerase, KlenTaq DNA polymerase, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, and a variant or derivative thereof.

In any of the embodiments herein, the amplification product can be generated in situ in the biological sample or in a matrix embedding the biological sample or molecules thereof. In some embodiments, the amplification product can be crosslinked to one or more other molecules in the biological sample and/or a matrix embedding the biological sample or molecules thereof.

In any of the embodiments herein, the method comprises detecting the amplification product in situ in the biological sample or in a matrix embedding the biological sample or molecules thereof.

In any of the embodiments herein, detecting the amplification product can comprise detecting a sequence in a loop region of a stem-loop structure in the amplification product. In some embodiments, the sequence in the loop region is a barcode sequence.

In any of the embodiments herein, detecting the amplification product can comprise contacting the biological sample with one or more detectably-labeled probes that directly or indirectly hybridize to one or more loop regions of the amplification product.

In any of the embodiments herein, a signal associated with the amplification product can be amplified in situ in the biological sample or in a matrix embedding the biological sample or molecules thereof. In some embodiments, the signal amplification comprises rolling circle amplification (RCA) of a probe that directly or indirectly binds to the amplification product; hybridization chain reaction (HCR) directly or indirectly on the amplification product; linear oligonucleotide hybridization chain reaction (LO-HCR) directly or indirectly on the amplification product; primer exchange reaction (PER) directly or indirectly on the amplification product; assembly of branched structures directly or indirectly on the amplification product; hybridization of a plurality of detectable probes directly or indirectly on the amplification product, or any combination thereof.

In any of the embodiments herein, the amplification product can be analyzed by sequential hybridization, sequencing by hybridization, sequencing by ligation, sequencing by synthesis, sequencing by binding, or a combination thereof.

In any of the embodiments herein, the amplification product can comprise one or more barcode sequences or complements thereof. In some embodiments, the one or more barcode sequences or complements thereof correspond to the target nucleic acid or a portion thereof.

In any of the embodiments herein, the one or more barcode sequences can be comprised by one or more loop regions of the amplification product. In some embodiments, at least two loop regions of the amplification product comprise barcode sequences.

In any of the embodiments herein, the same barcode sequence can be comprised by two loop regions of the amplification product.

In any of the embodiments herein, different barcode sequences can be

In any of the embodiments herein, the one or more barcode sequences or complements thereof can detected by: (i) contacting the biological sample with one or more detectably-labeled probes that directly or indirectly hybridize to the one or more barcode sequences or complements thereof, (ii) detecting signals associated with the one or more detectably-labeled probes, and (iii) dehybridizing the one or more detectably-labeled probes. In some embodiments, the contacting, detecting, and dehybridizing steps are repeated with the one or more detectably-labeled probes and/or one or more other detectably-labeled probes that directly or indirectly hybridize to the one or more barcode sequences or complements thereof.

Alternatively, In any of the embodiments herein, the one or more barcode sequences or complements thereof can be detected by: (i) contacting the biological sample with one or more intermediate probes that directly or indirectly hybridize to the one or more barcode sequences or complements thereof, wherein the one or more intermediate probes are detectable using one or more detectably-labeled probes, (ii) detecting signals associated with the one or more detectably-labeled probes, and (iii) dehybridizing the one or more intermediate probes and/or the one or more detectably-labeled probes. In some embodiments, the contacting, detecting, and dehybridizing steps are repeated with the one or more intermediate probes, the one or more detectably-labeled probes, one or more other intermediate probes, and/or one or more other detectably-labeled probes.

In any of the embodiments herein, the target nucleic acid can comprise DNA and/or RNA. In some embodiments, the target nucleic acid is genomic DNA/RNA, mRNA, cDNA, or a reporter oligonucleotide of a labelling agent that directly or indirectly binds to an analyte in the biological sample.

In any of the embodiments herein, the circular probe or circularizable probe or probe set can comprise DNA. In any of the embodiments herein, the circular probe or circularizable probe or probe set can comprise one or more ribonucleotides. In some embodiments, the circular probe or circularizable probe or probe set comprises no more than four consecutive ribonucleotides. In some embodiments, the one or more ribonucleotides are at and/or near a ligatable 3' end, optionally wherein the circularizable probe or probe set comprises a ribonucleotide at a 3' end.

In any of the embodiments herein, the stem regions of the first and second stem-loop structures independently can be between about 5 and about 15 bp in length. In some embodiments, the stem regions are independently about 6, about 7, about 8, about 9, or about 10 bp in length.

In any of the embodiments herein, the double stranded central structure can be between about 5 and about 15 bp in length. In some embodiments, the double stranded central structure is about 6, about 7, about 8, about 9, or about 10 bp in length.

In any of the embodiments herein, the loop regions of the first, second, third, and/or fourth stem-loop structures independently can be between about 5 and about 40 nucleotides in length. In some embodiments, the loop regions are independently between about 10 and about 20 nucleotides in length.

In any of the embodiments herein, the loop region of the first stem-loop structure can comprise a sequence that hybridizes to the target nucleic acid, and the loop region of the second, third, and/or fourth stem-loop structure can comprise one or more barcode sequences or complements thereof.

In any of the embodiments herein, the loop region of the second, third, or fourth stem-loop structure can comprise a primer binding sequence for initiating rolling circle amplification.

In any of the embodiments herein, the double stranded central structure can be between the stem regions of adjacent stem-loop structures and can be non-overlapping with the stem regions.

In any of the embodiments herein, each stem region can be or comprise a different sequence. In any of the embodiments herein, each stem region may not comprise a sequence that is complementary to a sequence in any other stem region. In any of the embodiments herein, each stem region may not comprise a sequence that is reverse complementary to a sequence in any other stem region. In any of the embodiments herein, two, three, four, or more of the stem regions can comprise a common sequence. In any of the embodiments herein, two stem regions can comprise the same sequence.

In any of the embodiments herein, stem regions of the third and fourth stem-loop structures can independently comprise (i) a sequence that hybridizes to an additional sequence of the target nucleic acid and/or (ii) one or more barcode sequences or complements thereof.

In any of the embodiments herein, the circularizable probe set can comprise two, three, or more probes.

In any of the embodiments herein, the amplification product can be in the form of a nanoball having a diameter of between about 0.1 µm and about 3 µm. In some embodiments, the diameter is between about 0.1 µm and about 0.5 µm, between about 0.5 µm and about 1 µm, between about 0.8 µm and about 1.3 µm, or between about 1 µm and about 1.5 µm. In some embodiments, the nanoball has a diameter of between about 0.8 µm and about 1.3 µm. In any of the embodiments herein, the reaction to generate the amplification product (e.g., RCA for generating an RCP) can be performed for about 30 minutes, about 1 hour, about 2 hours, about 3 hours, about 6 hours, about 12 hours, about 18 hours, about 24 hours, or longer.

In any of the embodiments herein, the amplification product can be between about 1 and about 15 kilobases, between about 15 and about 25 kilobases, between about 25 and about 35 kilobases, between about 35 and about 45 kilobases, between about 45 and about 55 kilobases, between about 55 and about 65 kilobases, between about 65 and about 75 kilobases, or more than 75 kilobases in length.

In any of the embodiments herein, the amplification product can comprise between about 10 and about 100, between about 100 and about 1,000, between about 1,000 and about 5,000, between about 5,000 and about 10,000, or more than 10,000 copies of the unit structure.

In any of the embodiments herein, the unit structure can comprise stem-loop and double stranded central structures that facilitate stacking of the multiple copies of the unit structure, thereby stabilizing and/or compacting the amplification product in situ in the biological sample or in a matrix embedding the biological sample or molecules thereof.

In any of the embodiments herein, the unit structure can comprise stem-loop and double stranded central structures that facilitate generation of a multi-unit structure comprising multiple copies of the unit structure around a central vertex, thereby stabilizing and/or compacting the amplification product in situ in the biological sample or in a matrix embedding the biological sample or molecules thereof. In some embodiments, the vertex comprises a sequence complementary to the primer binding sequence for initiating rolling circle amplification. In any of the embodiments herein, the multi-unit structure can comprises 3, 4, or 5 copies of the unit structure around a central vertex.

In any of the embodiments herein, steric hindrance between the multiple copies of the unit structure can facilitate stacking of multiple copies of the multi-unit structure, thereby stabilizing and/or compacting the amplification product in situ in the biological sample or in a matrix embedding the biological sample or molecules thereof.

In any of the embodiments herein, steric hindrance between the multiple copies of the unit structure can promotes compacting the amplification product in situ in the biological sample or in a matrix embedding the biological sample or molecules thereof.

In any of the embodiments herein, the method can further comprise crosslinking the amplification product to itself, to one or more other molecules in the biological sample, and/or to a matrix embedding the biological sample or molecules thereof. In some embodiments, the crosslinking reduces the mobility of the amplification product in the biological sample and/or in the matrix.

In some aspects, provided herein is a method for analyzing a biological sample, comprising: (a) contacting a biological sample with a circularizable probe or probe set that hybridizes to a target nucleic acid in the biological sample, wherein the circularizable probe or probe set comprises: a first stem-loop structure, a second stem-loop structure, a third stem-loop structure, a fourth stem-loop structure, and a double stranded central structure that is between the stem regions of adjacent stem-loop structures and is non-overlapping with the stem regions, and wherein the loop regions of the first, second, third, and/or fourth stem-loop structures independently comprise (i) a 5' end sequence and a 3' end sequence complementary to the target nucleic acid and/or (ii) one or more barcode sequences; (b) generating a circularized probe from the circularizable probe or probe set by ligating the 5' end sequence and the 3' end sequence hybridized to the target nucleic acid; (c) generating a rolling circle amplification (RCA) product using the circularized probe as a template, wherein the RCA product comprises multiple copies of a unit structure comprising complementary sequences of the first, second, third, and fourth stem-loop structures and the double stranded central structure; and (d) detecting the RCA product in situ in the biological sample and/or in a matrix embedding the biological sample or molecules thereof.

In some embodiments, the loop region of the first stem-loop structure comprises a 5' end sequence and a 3' end sequence complementary to the target nucleic acid, and generating the circularized probe can comprise, using the target nucleic acid as a template, ligating the 5' end and 3' end sequences in the loop region of the first stem-loop structure.

In any of the embodiments herein, the loop regions of the second, third, and fourth stem-loop structures can each comprise one or more barcode sequences corresponding to the target nucleic acid or a portion thereof.

In any of the embodiments herein, the loop regions of the first and second stem-loop structures can each comprise a 5' end sequence and a 3' end sequence complementary to the target nucleic acid, and generating the circularized probe can comprise, using the target nucleic acid as a template: (i) ligating the 5' end and 3' end sequences in the loop region of the first stem-loop structure and (ii) ligating the 5' end and 3' end sequences in the loop region of the second stem-loop structure.

In any of the embodiments herein, the loop regions of the third and fourth stem-loop structures can each comprise one or more barcode sequences corresponding to the target nucleic acid or a portion thereof.

In any of the embodiments herein, wherein the multiple copies of the unit structure can be stacked, thereby stabilizing and/or compacting the RCA product in situ in the biological sample and/or in the matrix.

In any of the embodiments herein, the biological sample can be a fixed and/or permeabilized biological sample.

In any of the embodiments herein, the biological sample can be a non-homogenized tissue sample or a tissue section. In some embodiments, the biological sample can be a formalin-fixed, paraffin-embedded (FFPE) tissue sample, a frozen tissue sample, or a fresh tissue sample. In some embodiments, the biological sample can be a tissue slice between about 1 μm and about 50 μm in thickness. In some embodiments, the tissue slice is between about 5 μm and about 35 μm in thickness.

In any of the embodiments herein, the biological sample can be crosslinked. In any of the embodiments herein, the biological sample can be embedded in a matrix. In some embodiments, the matrix is a hydrogel. In any of the embodiments herein, the biological sample can be cleared.

In some aspects, provided herein is a circular probe or circularizable probe or probe set, wherein the circular probe or circularizable probe or probe set comprises a first stem-loop structure, a second stem-loop structure, and a third stem-loop structure. In some embodiments, the circular probe or circularizable probe or probe set can comprise a double stranded central structure between the stem regions of the first and second stem-loop structures and the double stranded central structure is non-overlapping with the stem regions of the first, second, or third stem-loop structures. In some embodiments, the circular probe or circularizable probe or probe set comprises a fourth stem-loop structure. In some embodiments, a first strand of the double stranded central structure is between the stem regions of the first and second stem-loop structures and a second strand of the double stranded central structure is between the stem regions of the third and fourth stem-loop structures.

In some aspects, provided herein is a circular or circularizable probe or probe set, wherein the circular probe or circularizable probe or probe set comprises: (i) a first stem-loop structure, (ii) a second stem-loop structure, (iii) a third stem-loop structure, (iv) a fourth stem-loop structure, and (v) a double stranded central structure that is between the stem regions of adjacent stem-loop structures and is non-overlapping with the stem regions, and wherein the circular or circularizable probe or probe set is capable of hybridizing to a target nucleic acid in a biological sample. wherein each stem-loop structure comprises, from 5' to 3' a first stem sequence, a loop sequence, and a second stem sequence, wherein the second stem sequence comprises a reverse complement sequence of the first stem sequence.

In some aspects, provided herein is a kit comprising the circular or circularizable probe or probe set, such as any of the circular or circularizable probes or probe sets described in Section III.

In some embodiments, provided herein is an amplification product comprising multiple copies of a unit structure comprising complementary sequences of circular or circularizable probe or probe set, such as any of the amplification products described in Section IV.

In any of the embodiments herein, the loop regions of the first, second, third, and/or fourth stem-loop structures can independently comprise (i) a 5' end sequence and a 3' end sequence complementary to the target nucleic acid and/or (ii) one or more barcode sequences. In some embodiments the kit further comprises one or more detection probes that hybridize to the one or more barcode sequences. In any of comprising instructions for performing the method of any of any of the preceding embodiments.

BRIEF DESCRIPTION OF THE DRAWINGS

The drawings illustrate certain embodiments of the features and advantages of this disclosure. These embodiments are not intended to limit the scope of the appended claims in any manner.

As shown in FIG. 1A, in some embodiments, a circularizable probe disclosed herein comprises a first stem-loop structure, a second stem-loop structure, a third stem-loop structure, and a fourth stem-loop structure. In some embodiments, each of the stem-loop structures comprises a distinct stem sequence (e.g., complementary sequences hybridize to form the stem). In some embodiments, two stem-loop structures can comprise the same stem sequence. In some embodiments, the first loop region comprises a sequence that hybridizes to a sequence of the target nucleic acid, optionally wherein the loop region comprises a ligation site that is ligated using the target nucleic acid as a template. The second, third, and fourth loops can comprise one or more barcode sequence(s) or complements thereof, and/or one or more primer binding sequences and/or anchor binding sequences. As shown in FIG. 1B, in some embodiments, the circularizable probe or probe set comprises two or more nucleic acid molecules that can be ligated to generate a circularized probe. In some embodiments, a first loop of the circularizable probe set hybridizes to a first sequence of the target nucleic acid, and a second loop of the circularizable probe set hybridizes to a second sequence of the target nucleic acid. In some embodiments, the first loop and the second loop comprise a first and second ligation site that are ligated using the target nucleic acid as a template.

FIGS. 2A-2B show an exemplary probe design for linear expansion of a unit structure. As shown in FIG. 2A, "linear expansion" can describe expansion of an amplification product comprising multiple unit structures (e.g., a single hairpin unit structure), wherein the size, shape and/or flexibility of the unit structures does not cause sufficient steric hindrance between the unit structures to promote radial expansion around a vertex and/or stacking of unit structures. For example, in some embodiments, a circular or circularized probe comprising a single stem-loop structure can be amplified to generate an amplification product comprising multiple copies of a single stem-loop unit structure connected by linkers, wherein the linker sequence is complementary to a loop of the circular or circularized probe. In some embodiments, the shape and/or size of the stem-loop structure allows formation of a linear and/or flexible chain of stem-loop structures.

FIGS. 2C-2D show exemplary probe designs for radial expansion and/or stacking of unit structures. As shown in FIG. 2C, in some embodiments, a larger and/or more rigid unit structure can result in steric hindrance between multiple unit structures in an amplification product, wherein steric hindrance between unit structures promotes radial expansion (e.g., generation of multiple unit structures around a central vertex) and/or stacking of multiple unit structures (e.g., rotation of a unit structure relative to a linker sequence, such that multiple unit structures are stacked in the amplification product. As shown in FIG. 2D, in some embodiments, a circular or circularizable probe or probe set disclosed herein comprises two, three, four, or more stem-loop structures. In some embodiments, a circular or circularizable probe or probe set further comprises a double stranded central structure.

DETAILED DESCRIPTION

Figures 1A, 1B:
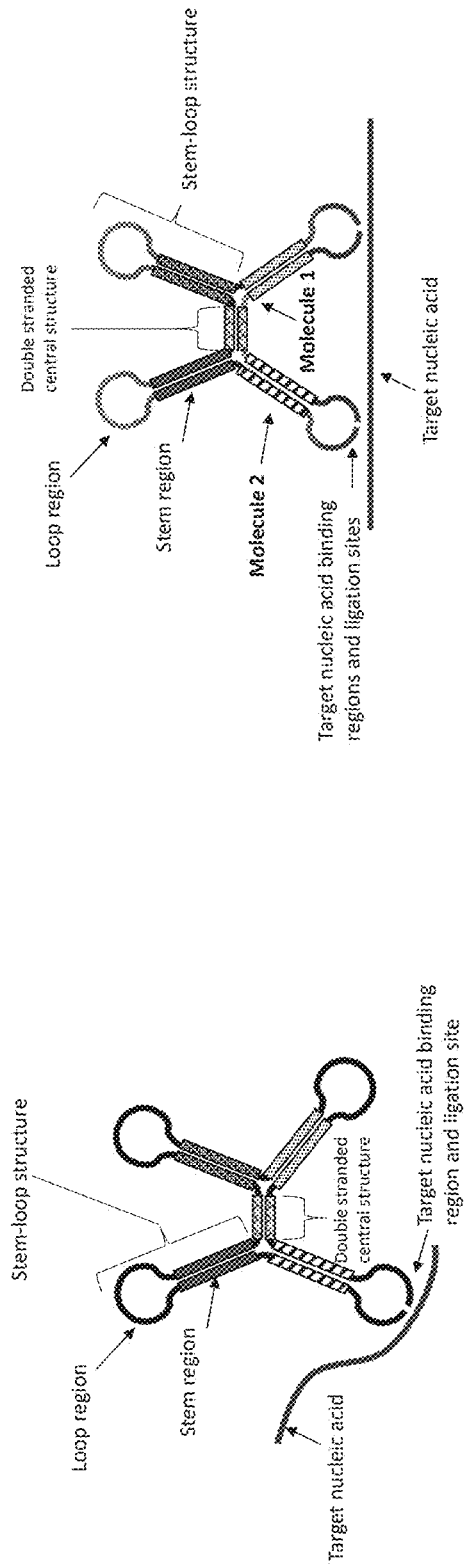
FIGS. 1A-1B depict exemplary designs of circular or circularizable probes or probe sets provided herein.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

In some aspects, provided herein are circular probes or circularizable probes or probe sets that facilitate generation of compacted rolling circle amplification (RCA) products (RCP). When utilizing rolling circle amplification (RCA) to detect nucleic acid targets, properly resolving densely packed rolling circle amplification products (RCPs) in a cell or surface depends upon resolution of the individual RCPs. RCPs are concatemers comprising multiple copies of the RCA probe sequence, which can be visualized using in situ detection probes. RCP detection is enhanced by compaction of the concatemers, as reduction in size results in local concentration of the detection probes to increase signal intensity. Compaction also allows for increased resolution of individual RCPs. Existing strategies for compaction of RCPs rely on hybridization of linear compaction probes (e.g., as described by Clausson et al. *Sci Rep* 5, 12317 (2015)). However, linear compaction probes are typically stripped away along with detection probes following rounds of in situ hybridization and target detection. Thus, there is a need for methods and compositions for persistent compaction of RCPs that are resistant to stripping and/or that do not require the use of additional probes distinct from the circular or circularizable probes used in RCA.

In some aspects, a circular or circularizable probe or probe set provided herein comprises a unit structure (e.g., a unit structure comprising a first stem-loop structure, a second stem-loop structure, and a third stem-loop structure). In some embodiments, methods provided herein comprise generating an amplification product using the circular probe or a circularized probe generated from the circularizable probe or probe set as a template, wherein the amplification product comprises multiple copies of the unit structure (e.g., a unit structure comprising complementary sequences of the first stem-loop structure, second stem-loop structure, and third stem-loop structure). In some aspects, the formation of multiple copies of the unit structure promotes compaction of the RCP. In some embodiments, the formation of multiple copies of the unit structure promotes stacking and/or radial expansion (e.g., expansion of multiple copies of a unit structure radially around a central vertex) of the unit structures, thereby stabilizing and/or compacting the amplification product in situ in the biological sample or in a matrix embedding the biological sample or molecules thereof.

In some aspects, the circular or circularizable probe set comprises a first stem-loop structure, a second stem-loop structure, and a third stem-loop structure, and the amplification product comprises multiple copies of a unit structure comprising complementary sequences of the first stem-loop structure, the second stem-loop structure, and the third stem-loop structure. In some embodiments, the circular probe or circularizable probe or probe set comprises a double stranded central structure between the stem regions of the first and second stem-loop structures, and the double stranded central structure is non-overlapping with the stem regions of the first, second, or third stem-loop structures. Thus, in some embodiments, the unit structure of the amplification product comprises a complementary sequence of the double stranded central structure. In some embodiments, the circular or circularizable probe further comprises a fourth stem-loop structure, and the unit structure of the amplification product comprises complementary sequences to the fourth stem-loop structure. In some embodiments, the presence of multiple stem-loop structures in the unit structure promotes compaction of the amplification product (e.g., by promoting stacking and/or radial expansion of multiple unit structures of the amplification product). In some embodiments, the double stranded central structure stabilizes the unit structure and/or preserves the shape of the unit structure. In some embodiments, the double stranded central structure reduces or prevents twisting of one or more stem-loop structures relative to another stem-loop structure within the unit structure. In some embodiments, steric hindrance between multiple copies of the unit structure facilitates the stacking and/or radial expansion of multiple unit structures. In some embodiments, the double stranded central structure allows the structure to fold back in on itself (e.g., promotes folding of the stem-loop structures to form the unit structure).

In some embodiments, steric hindrance between multiple copies of the unit structure promotes radial expansion of multiple unit structures (e.g., formation of a multi-unit structure comprising multiple copies of the unit structure around a central vertex) followed by stacking of multiple multi-unit structures. In some embodiments, the amplification product comprises a stack of multi-unit structures, wherein each multi-unit structure comprises 2, 3, 4, 5, or 6 copies of the unit structure around a central vertex.

In some aspects, the circular probe or circularizable probe or probe set designs disclosed herein facilitate generation of an RCP wherein one or more barcode sequences comprised by the RCP are oriented on the outside of the RCP. For example, in some embodiments, the amplification product comprises multiple unit structures comprising stem-loop structures, wherein one or more loop regions comprise one or more barcode sequences or complements thereof. In some embodiments, the one or more unit structures form multi-unit structures wherein one or more loop regions are oriented toward the outside of the multi-unit structure (e.g., around a central vertex). In some embodiments, the central vertex comprises a sequence complementary to a primer binding site comprised by a loop region of the circular probe or circularizable probe or probe set, and the loop region(s) comprising the barcode sequence(s) are oriented toward the outside of the multi-unit structure. Thus, in some aspects, the probe designs and methods provided herein enable enhanced detection of the RCP product (e.g., by making barcode sequences more accessible in rolling circle amplification product comprising multiple unit structures).

Provided herein are methods involving the use of one or more probes (e.g., a circular probe or circularizable probe or probe set as described in Section III) for analyzing one or more target nucleic acid(s), such as a target nucleic acid (for example, a messenger RNA) present in a cell or a biological sample, such as a tissue sample. Also provided are probes, sets of probes, compositions, kits, systems and devices for use in accordance with the provided methods. In some aspects, the provided methods and systems can be applied to detect, image, quantitate, or determine the presence or absence of one or more target nucleic acid(s) or portions thereof (e.g., presence or absence of sequence variants such as point mutations and SNPs). In some aspects, the provided methods can be applied to detect, image, quantitate, or determine the sequence of one or more target nucleic acid(s), comprising sequence variants such as point mutations and SNPs.

In some aspects, the provided embodiments can be employed for in situ detection and/or sequencing of a target nucleic acid in a cell, e.g., in cells of a biological sample or a sample derived from a biological sample, such as a tissue section on a solid support, such as on a transparent slide.

In some aspects, provided herein are in situ assays using microscopy as a readout, e.g., nucleic acid sequencing, hybridization, or other detection or determination methods involving an optical readout. In some aspects, detection or determination of a sequence of one, two, three, four, five, or more nucleotides of a target nucleic acid is performed in situ in a cell in an intact tissue. In some aspects, detection or determination of a sequence is performed such that the localization of the target nucleic acid (or product or a derivative thereof associated with the target nucleic acid) in the originating sample is detected. In some embodiments, the assay comprises detecting the presence or absence of an amplification product or a portion thereof (e.g., RCA product). In some embodiments, a method for spatially profiling analytes such as the transcriptome or a subset thereof in a biological sample is provided. Methods, compositions, kits, devices, and systems for these in situ assays, comprising spatial genomics and transcriptomics assays, are provided. In some embodiments, a provided method is quantitative and preserves the spatial information within a tissue sample without physically isolating cells or using homogenates.

Nucleic acids and/or analytes that can be analyzed by the presently disclosed methods are described in greater detail in Section II.

II. Samples, Analytes, and Target Sequences

A method disclosed herein may be used to process and/or analyze any analyte(s) of interest, for example, for detecting the analyte(s) in situ in a sample of interest. A target nucleic acid sequence as disclosed herein may be or be comprised in an analyte (e.g., a nucleic acid analyte, such as genomic DNA, mRNA transcript, or cDNA, or a product thereof, e.g., an extension or amplification product, such as an RCA product) and/or may be or be comprised in a labelling agent for one or more analytes (e.g., a nucleic acid analyte or a non-nucleic acid analyte) in a sample or a product of the labelling agent. Exemplary analytes and labelling agents are described below.

A. Samples

A sample disclosed herein can be or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells that are deposited on a surface.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and that allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 µm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 µm. Thicker sections can also be used if desired or convenient, e.g., at least 70, 80, 90, or 100 µm or more. Typically, the thickness of a tissue section is between 1-100 µm, 1-50 µm, 1-30 µm, 1-25 µm, 1-20 µm, 1-15 µm, 1-10 µm, 2-8 µm, 3-7 µm, or 4-6 µm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or circularizable probe or probe set. In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a circularizable probe or probe set.

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method.

Methods for embedding a sample in a matrix have been described in, e.g., US2016/0024555 and WO2018/089438, which are incorporated herein by reference in their entirety. In some embodiments, the hydrogel comprises a three dimensional matrix. For example, the matrix may be a three dimensional nucleic acid-containing polymer. In some embodiments, the polymer is a gel or a hydrogel. In some embodiments, the nucleic acids described herein (e.g., circular or circularizable probes or probe sets or amplification products thereof) may be bound a hydrogel matrix to stabilize an amplification product in the sample.

In some embodiments, the matrix may encapsulate a biological sample, such as a tissue sample. In some embodiments, the sample is embedded or immobilized, partially or completely, in the matrix. In some embodiments, the matrix comprises polyacrylamide, cellulose, alginate, polyamide, cross-linked agarose, cross-linked dextran or cross-linked polyethylene glycol. In some embodiments, the matrix comprises any suitable polymerizing and/or crosslinking material. In some embodiments, polymerization initiators and/or crosslinkers may be present. In some embodiments, the matrix is porous, such that exogenous reagents and/or oligonucleotide probes described herein may be introduced to the matrix.

In some aspects, a circular probe, circularizable probe or probe set, or an amplification product described herein bound to the three dimensional matrix comprises naturally or non-naturally occurring nucleic acids (e.g., synthetic or modified nucleic acids). In some embodiments, a primer for initiation of rolling circle amplification is modified to incorporate a functional moiety for attachment to the matrix (such as, by covalent cross-linking or non-covalent binding). In some embodiments, the functional moiety is bound to the oligonucleotide probe at the 5' end of the probe. In some embodiments, the cross-linker reactive group is any suitable reactive group.

In some embodiments, the matrix is modified to incorporate a functional moiety for attachment to a probe, probe set, or amplification product provided herein. In some embodiments, a functional moiety of a probe, probe set, or amplification product is attached (e.g., by covalent cross-linking or non-covalent binding) to the matrix via the functional group of the matrix. In some embodiments, the cross-linkers further include a spacer for attachment to the matrix. In some embodiments, the spacer comprises polyethylene glycol, carbon spacers, and/or photo-cleavable spacers.

The functional moiety of the oligonucleotide probe and/or the matrix may comprise a ligand. In some embodiments, the ligand reacts with a cross-linker or another ligand (e.g., the ligand of the oligonucleotide probe reacts with the ligand of the matrix). In some embodiments, the functional moiety is any of an amine, acrydite, alkyne, biotin, azide, and thiol. In some embodiments, the method comprises embedding an oligonucleotide probe comprising a functional moiety described herein to the matrix. In some embodiments, the functional moiety of the matrix is an alkyne, and the functional moiety of the oligonucleotide probe is an azide.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample comprises cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 m to about 2 mm.

Additional methods and aspects of hydrogel embedding of biological samples are described for example in Chen et al., *Science* 347(6221):543-548, 2015, the entire contents of which are incorporated herein by reference.

(v) Staining

To facilitate visualization, biological samples can be stained using a wide variety of stains and staining techniques. In some embodiments, for example, a sample can be stained using any number of stains and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g, DiI, DiO, DiR, DiD). Other cell membrane stains may include FM and RH dyes or immunohistochemical reagents specific for cell membrane proteins. In some examples, the stain may include, but not limited to, acridine orange, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Methods of destaining or discoloring a biological sample generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347(6221):543-548, 2015.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly cross-linked prior to or during an in situ assay round. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively by any other hydrogel-formation. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(viii) Tissue Permeabilization and Treatment

In some embodiments, a biological sample can be permeabilized to facilitate transfer of analytes out of the sample, and/or to facilitate transfer of species (such as probes) into the sample. If a sample is not permeabilized sufficiently, the amount of species (such as probes) in the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to opening up DNA in a cell for hybridization by a probe. For example, proteinase K treatment may be used to free up DNA with proteins bound thereto.

(ix) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, thereby selectively enriching these RNAs.

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics*, 15 401, (2014), the entire contents of which are incorporated herein by reference). Furthermore, hydroxyapatite chromatography can remove abundant species (e.g., rRNA) (see, e.g., Vandernoot, V. A., cDNA normalization by hydroxyapatite chromatography to enrich transcriptome diversity in RNA-seq applications, *Biotechniques*, 53(6) 373-80, (2012), the entire contents of which are incorporated herein by reference).

A biological sample may comprise one or a plurality of analytes of interest. Methods for performing multiplexed assays to analyze two or more different analytes in a single biological sample are provided.

B. Analytes

The methods and compositions disclosed herein can be used to detect and analyze a wide variety of different analytes. In some aspects, an analyte can include any biological substance, structure, moiety, or component to be analyzed. In some aspects, a target disclosed herein may similarly include any analyte of interest. In some examples, a target or analyte can be directly or indirectly detected.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a macromolecule such as a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template (e.g., a circular probe or circularizable probe or probe set disclosed herein, such as those described in Section III). Alternatively, the specific binding partner may be coupled to a nucleic acid, which may be detected using an RCA strategy, e.g. in an assay that uses or generates a circular nucleic acid molecule, which can be the RCA template.

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

(i) Endogenous Analytes

In some embodiments, an analyte herein is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labelling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any embodiment described herein, the analyte comprises a target sequence. In some embodiments, the target sequence may be endogenous to the sample, generated in the sample, added to the sample, or associated with an analyte in the sample. In some embodiments, the target sequence is a single-stranded target sequence (e.g., a sequence in a rolling circle amplification product). In some embodiments, the analytes comprise one or more single-stranded target sequences. In one aspect, a first single-stranded target sequence is not identical to a second single-stranded target sequence. In another aspect, a first single-stranded target sequence is identical to one or more second single-stranded target sequence. In some embodiments, the one or more second single-stranded target sequence is comprised in the same analyte (e.g., nucleic acid) as the first single-stranded target sequence. Alternatively, the one or more second single-stranded target sequence is comprised in a different analyte (e.g., nucleic acid) from the first single-stranded target sequence.

(ii) Labelling Agents

In some embodiments, provided herein are methods and compositions for analyzing endogenous analytes (e.g., RNA, ssDNA, and cell surface or intracellular proteins and/or metabolites) in a sample using one or more labelling agents. In some embodiments, an analyte labelling agent may include an agent that interacts with an analyte (e.g., an endogenous analyte in a sample). In some embodiments, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some embodiments, the analyte labelling agent comprises an analyte binding moiety and a labelling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method comprises one or more post-fixing (also referred to as post-fixation) steps after contacting the sample with one or more labelling agents.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, e.g., a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labelling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labelling agents are the same. In some embodiments in which the plurality of analytes includes a single species of analyte, the analyte binding moieties of the plurality of analyte labelling agents are the different (e.g., members of the plurality of analyte labelling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing.

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (i.e., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labelling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

(iii) Products of Endogenous Analyte and/or Labelling Agent

In some embodiments, provided herein are methods and compositions for analyzing one or more products of an endogenous analyte and/or a labelling agent in a biological sample. In some embodiments, an endogenous analyte (e.g., a viral or cellular DNA or RNA) or a product (e.g., a hybridization product, a ligation product, an extension product (e.g., by a DNA or RNA polymerase), a replication product, a transcription/reverse transcription product, and/or an amplification product such as a rolling circle amplification (RCA) product) thereof is analyzed. In some embodiments, a labelling agent that directly or indirectly binds to an analyte in the biological sample is analyzed. In some embodiments, a product (e.g., a hybridization product, a ligation product, an extension product (e.g., by a DNA or RNA polymerase), a replication product, a transcription/reverse transcription product, and/or an amplification product such as a rolling circle amplification (RCA) product) of a labelling agent that directly or indirectly binds to an analyte in the biological sample is analyzed.

(a) Hybridization

In some embodiments, a product of an endogenous analyte and/or a labelling agent is a hybridization product comprising the pairing of substantially complementary or complementary nucleic acid sequences within two different molecules, one of which is the endogenous analyte or the labelling agent (e.g., reporter oligonucleotide attached thereto). The other molecule can be another endogenous molecule or another labelling agent such as a probe. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another. Various probes and probe sets can be hybridized to an endogenous analyte and/or a labelling agent and each probe may comprise one or more barcode sequences. In some embodiments, a circular probe or circularizable probe or probe set as described in Section III is hybridized to a sequence of a target nucleic acid (e.g., an endogenous analyte such as an RNA, e.g., an mRNA) in the biological sample.

(b) Ligation

In some embodiments, a product of an endogenous analyte and/or a labelling agent is a ligation product. In some embodiments, the ligation product is formed between two or more endogenous analytes. In some embodiments, the ligation product is formed between an endogenous analyte and a labelling agent. In some embodiments, the ligation product is formed between two or more labelling agent. In some embodiments, the ligation product is an intramolecular ligation of an endogenous analyte. In some embodiments, the ligation product is an intramolecular ligation of a labelling agent, for example, the circularization of a circularizable probe or probe set upon hybridization to a target sequence. The target sequence can be comprised in an endogenous analyte (e.g., nucleic acid such as a genomic DNA or mRNA) or a product thereof (e.g., cDNA from a cellular mRNA transcript), or in a labelling agent (e.g., the reporter oligonucleotide) or a product thereof. In some embodiments, a circular probe or circularizable probe or probe set as described in Section III hybridized to a sequence of a target nucleic acid (e.g., an endogenous analyte such as an RNA, e.g., an mRNA) in the biological sample is ligated to generate a circular template for generating an amplification product, such as an RCA product.

In some embodiments, provided herein is a probe or probe set capable of DNA-templated ligation, such as from a cDNA molecule. See, e.g., U.S. Pat. No. 8,551,710, which is hereby incorporated by reference in its entirety. In some embodiments, provided herein is a probe or probe set capable of RNA-templated ligation. See, e.g., U.S. Pat. Pub. 2020/0224244 which is hereby incorporated by reference in its entirety. In some embodiments, the probe set is a SNAIL probe set. See, e.g., U.S. Pat. Pub. 20190055594, which is hereby incorporated by reference in its entirety. In some embodiments, provided herein is a multiplexed proximity ligation assay. See, e.g., U.S. Pat. Pub. 20140194311 which is hereby incorporated by reference in its entirety. In some embodiments, provided herein is a probe or probe set capable of proximity ligation, for instance a proximity ligation assay for RNA (e.g., PLAYR) probe set. See, e.g., U.S. Pat. Pub. 20160108458, which is hereby incorporated by reference in its entirety. In some embodiments, a circular probe can be indirectly hybridized to the target nucleic acid. In some embodiments, the circular construct is formed from a probe set capable of proximity ligation, for instance a proximity ligation in situ hybridization (PLISH) probe set. See, e.g., U.S. Pat. Pub. 2020/0224243 which is hereby incorporated by reference in its entirety.

In some embodiments, the ligation involves chemical ligation. In some embodiments, the ligation involves template dependent ligation. In some embodiments, the ligation involves template independent ligation. In some embodiments, the ligation involves enzymatic ligation.

In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as E. coli DNA ligase, Tth DNA ligase, Thermococcus sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, i.e., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, a circular or circularizable probe or probe set (e.g., described in Section III), or a target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling, for example, by Mu polymerase, DNA polymerase, RNA polymerase, reverse transcriptase, VENT polymerase, Taq polymerase, and/or any combinations, derivatives, and variants (e.g., engineered mutants) thereof. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some embodiments, the ligation herein is a proximity ligation of ligating two (or more) nucleic acid sequences that are in proximity with each other, e.g., through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(c) Primer Extension and Amplification

In some embodiments, a product is a primer extension product of an analyte, a labelling agent, a probe or probe set bound to the analyte (e.g., a circular or circularizable probe or probe set bound to genomic DNA, mRNA, or cDNA), or a probe or probe set bound to the labelling agent (e.g., a circular or circularizable probe or probe set bound to one or more reporter oligonucleotides from the same or different labelling agents).

A primer is generally a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence. A primer extension reaction generally refers to any method where two nucleic acid sequences become linked (e.g., hybridized) by an overlap of their respective terminal complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

In some embodiments, a product of an endogenous analyte and/or a labelling agent is an extension or amplification product of one or more polynucleotides, for instance, a circular probe or circularizable probe or probe set. In some embodiments, the amplifying is achieved by performing rolling circle amplification (RCA). In other embodiments, a primer that hybridizes to the circular probe or circularized probe is added and used as such for amplification. In some embodiments, the RCA comprises a linear RCA, a branched RCA, a dendritic RCA, or any combination thereof.

In some embodiments, the extension or amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (i.e., amplicon) containing multiple copies of the cDNA. Techniques for rolling circle amplification (RCA) such as linear RCA, a branched RCA, a dendritic RCA, or any combination thereof. (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29:el 18, 2001; Dean et al. Genome Res. 1 1:1095-1099, 2001; Schweitzer et al, Nature Biotech. 20:359-365, 2002; U.S. Pat. Nos. 6,054,274, 6,291,187, 6,323,009, 6,344,329 and 6,368,801). Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix. Exemplary modification and polymer matrix that can be employed in accordance with the provided embodiments comprise those described in, for example, WO 2014/163886, WO 2017/079406, US 2016/0024555, US 2018/0251833 and US 2017/0219465. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

In some embodiments, the RCA template may comprise the target analyte, or a part thereof, where the target analyte is a nucleic acid, or it may be provided or generated as a proxy, or a marker, for the analyte. As noted above, many assays are known for the detection of numerous different analytes, which use a RCA-based detection system, e.g., where the signal is provided by generating a RCP from a circular RCA template which is provided or generated in the assay, and the RCP is detected to detect the analyte. The RCP may thus be regarded as a reporter which is detected to detect the target analyte. However, the RCA template may also be regarded as a reporter for the target analyte; the RCP is generated based on the RCA template, and comprises complementary copies of the RCA template. The RCA template determines the signal which is detected, and is thus indicative of the target analyte. As will be described in more detail below, the RCA template may be a probe, or a part or component of a probe, or may be generated from a probe, or it may be a component of a detection assay (i.e. a reagent in a detection assay), which is used as a reporter for the assay, or a part of a reporter, or signal-generation system. The RCA template used to generate the RCP may thus be a circular (e.g. circularized) reporter nucleic acid molecule, namely from any RCA-based detection assay which uses or generates a circular nucleic acid molecule as a reporter for the assay. Since the RCA template generates the RCP reporter, it may be viewed as part of the reporter system for the assay.

In some embodiments, a product herein includes a molecule or a complex generated in a series of reactions, e.g., hybridization, ligation, extension, replication, transcription/reverse transcription, and/or amplification (e.g., rolling circle amplification), in any suitable combination. For example, a product comprising a target sequence for a probe disclosed herein (e.g., a probe comprising the hybridizing region comprising one or more photoreactive nucleotides) may be a hybridization complex formed of a cellular nucleic acid in a sample and an exogenously added nucleic acid probe. The exogenously added nucleic acid probe may comprise an overhang that does not hybridize to the cellular nucleic acid but hybridizes to another probe. The exogenously added nucleic acid probe may be optionally ligated to a cellular nucleic acid molecule or another exogenous nucleic acid molecule. In other examples, a product comprising a target sequence for a probe disclosed herein may be an RCP of a circularizable probe or probe set which hybridizes to a cellular nucleic acid molecule (e.g., genomic DNA or mRNA) or product thereof (e.g., a transcript such as cDNA, a DNA-templated ligation product of two probes, or an RNA-templated ligation product of two probes). In other examples, a product comprising a target sequence for a probe disclosed herein may a probe hybridizing to an RCP. The probe may comprise an overhang that does not hybridize to the RCP but hybridizes to another probe. The probe may be optionally ligated to a cellular nucleic acid molecule or another probe, e.g., an anchor probe that hybridize to the RCP.

C. Target Sequences

A target sequence for a probe (e.g., a circular probe or circularizable probe or probe set) disclosed herein may be comprised in any analyte disclose herein, including an endogenous analyte (e.g., a viral or cellular nucleic acid), a labelling agent, or a product of an endogenous analyte and/or a labelling agent.

In some aspects, one or more of the target sequences includes a region of interest that can be detected using a circular or circularizable probe or probe set herein. In some embodiments, ligation and/or amplification of a circular or circularizable probe or probe set depends on hybridization of the circular or circularizable probe or probe set to the region of interest (e.g., depends on the presence of a sequence complementary to the region of interest of the target nucleic acid in the circular or circularizable probe or probe set). In some embodiments, the region of interest is a single nucleotide (e.g., a SNP). In some embodiments, the region of interest comprises 2, 3, 4, 5, 6, 7, 8, 9, 10, or more nucleotides. In some embodiments, the sequence complementary to the region of interest is located at or adjacent to a ligatable end of the circularizable probe or probe set. In some embodiments, the sequence complementary to the region of interest is located at a 3' end of the circularizable probe or probe set.

In some aspects, one or more of the target sequences includes one or more barcode(s), e.g., at least two, three, four, five, six, seven, eight, nine, ten, or more barcodes. Barcodes can spatially-resolve molecular components found in biological samples, for example, within a cell or a tissue sample. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In any of the embodiments herein, barcodes (e.g., barcode sequences of circular or circularizable probes or probe sets) can be analyzed (e.g., detected or sequenced) using any suitable methods or techniques, including those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), in situ sequencing, hybridization-based in situ sequencing (HybISS), targeted in situ sequencing, fluorescent in situ sequencing (FISSEQ), sequencing by synthesis (SBS), sequencing by ligation (SBL), sequencing by hybridization (SBH), or spatially-resolved transcript amplicon readout mapping (STARmap). In any of the embodiments herein, the methods provided herein can include analyzing the barcodes by sequential hybridization and detection with a plurality of labelled probes (e.g., detection oligos).

In some embodiments, in a barcode sequencing method, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises $4^N$ Complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5$=1024), whereas 8 nucleotide barcodes can be used to identify up to 65,536 molecular species, a number greater than the total number of distinct genes in the human genome. In some embodiments, the barcode sequences contained in the probes or RCPs are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 20190055594 and WO2019199579A1, which are hereby incorporated by reference in their entirety.

III. Circularizable Probe or Probe Set Design

In some aspects, the present disclosure provides methods for stabilizing and/or compacting a nucleic acid concatemer for in situ analyses. In some embodiments, methods disclosed herein are useful for the stabilization and/or compaction of nucleic acid concatemers in a biological sample, which provides advantages for downstream in situ analyses (e.g., target sequence detection).

In some aspects, provided herein is a method for analyzing a biological sample, comprising: (a) hybridizing a circular probe or circularizable probe or probe set to a sequence of a target nucleic acid in the biological sample, and (b) generating an amplification product using the circular probe or a circularized probe generated from the circularizable probe or probe set as a template, wherein the amplification product comprises multiple copies of a unit structure comprising complementary sequences of the circular probe or circularizable probe or probe set. In some embodiments, the amplification product comprising multiple copies of the unit structure is intact and the multiple copies of the unit structure is detected while connected to each other. In some embodiments, the amplification product does not comprise digestion sites (e.g., restriction digestion sites). In some cases, the unit structures are not separated from each other prior to detection.

In some embodiments, the circular probe or circularizable probe or probe set comprises a stem-loop structure, and the unit structure of the amplification product comprises a stem-loop structure. In some examples, the first, second, and third stem-loop structure of each unit structure comprises a stem region comprising complementary sequences within each stem-loop structure. In some embodiments, the circular probe or circularizable probe or probe set comprises one, 2, 3, 4, 5, 6, or more stem-loop structures (e.g., as shown in FIG. 2B or FIG. 2D). In some embodiments, the circular probe or circularizable probe or probe set comprises one stem-loop structure. In some embodiments, the circular probe or circularizable probe or probe set comprises two stem-loop structures. In some embodiments, the circular probe or circularizable probe or probe set comprises three stem-loop structures. In some embodiments, the circular probe or circularizable probe or probe set comprises four stem-loop structures. In some embodiments, the circular probe or circularizable probe or probe set comprises more than four (e.g., 5, 6, or more) stem-loop structures.

Figure 3:
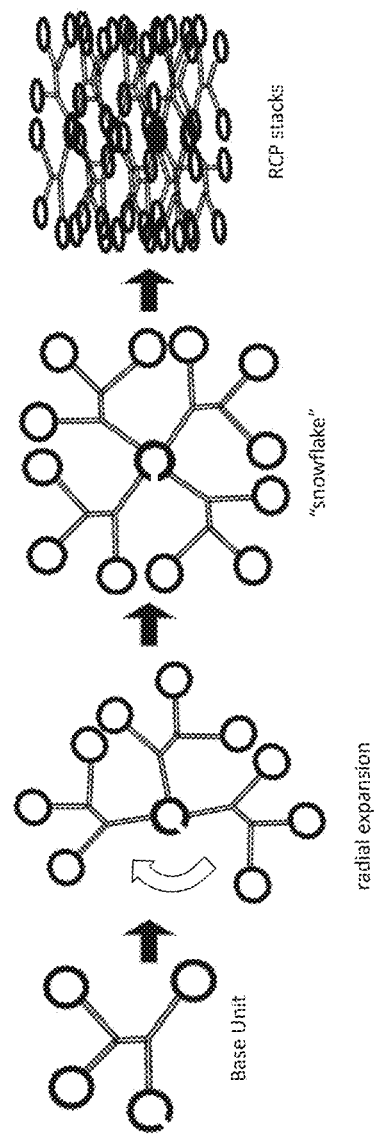
FIG. 3 shows an example of radial expansion and stacking to facilitate compaction of a rolling circle amplification product. In some embodiments, the generation of an amplification product comprising multiple copies of a unit structure (e.g., a unit structure comprising a first stem-loop structure, a second stem-loop structure, a third stem-loop structure, a fourth stem-loop structure, and a double stranded central region comprising a first strand between the first stem-loop structure and the second stem-loop structure, and a second strand between the third stem-loop structure and a fourth stem-loop structure). In some embodiments, the amplification step comprises generating a multi-unit structure comprising multiple copies of the unit structure around a central vertex. In some embodiments, the amplification step further comprises generating stacks of the multi-unit structure. In some embodiments, the central vertex of the multi-unit structure comprises a sequence complementary to a loop region of the circular or circularizable probe comprising a primer binding site. In some embodiments, one or more of the other loop regions of the unit structure are oriented on the outside of the multi-unit structure.
Figure 4A:
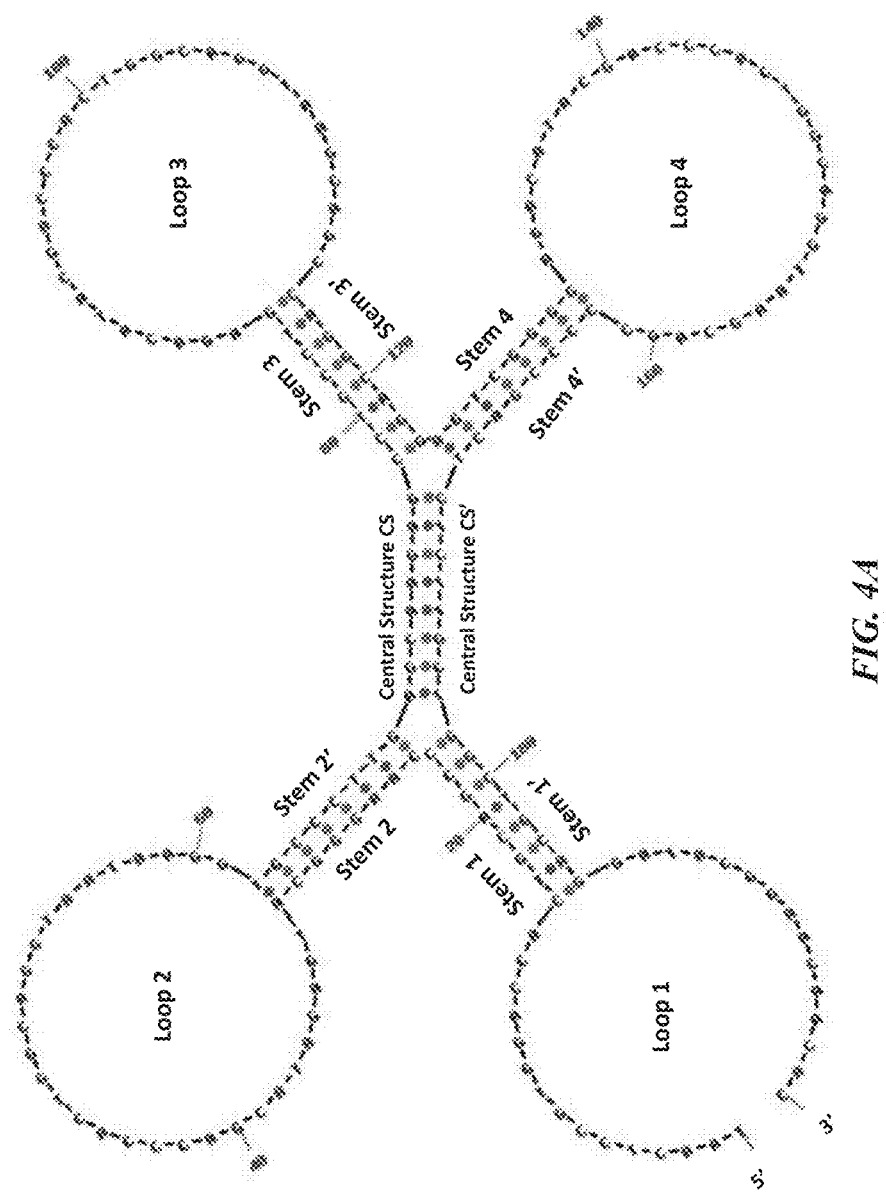
FIGS. 4A-4B shows the sequence and secondary structures of an exemplary circularizable probe. The exemplary structure is shown in FIG. 4A, and the annotated sequence (SEQ ID NO: 1) is shown in FIG. 4B. The 5' and 3' ends of the probe are in the loop region (Loop 1) of a first stem-loop structure and comprise RNA binding sequences that hybridize to an mRNA transcript of a gene. The probe can be circularized using the mRNA sequence as a template. The second, third, and fourth stem-loop structures each comprises a gene specific barcode sequence in the loop region (Loop 2, Loop 3, and Loop 4). The stem region sequences (Stem) and central structure sequences (CS) are also indicated. Stem 1' is a reverse complement of Stem 1; Stem 2' is a reverse complement of Stem 2; Stem 3' is a reverse complement of Stem 3; Stem 4' is a reverse complement of Stem 4; and CS' is a reverse complement of CS.
Figure 4B:
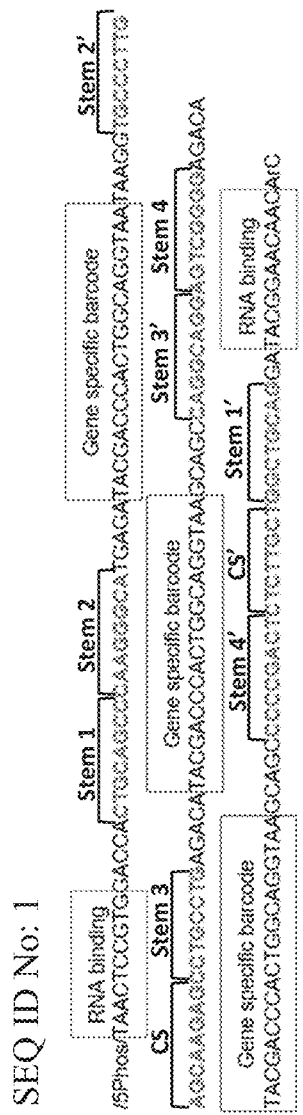

In some embodiments, the unit structure comprised by the amplification product comprises one, 2, 3, 4, 5, 6, or more stem-loop structures (e.g., as shown in FIG. 2B or FIG. 3). In some embodiments, the unit structure comprised by the amplification product comprises one stem-loop structure. In some embodiments, the unit structure comprised by the amplification product comprises two stem-loop structures. In some embodiments, the unit structure comprised by the amplification product comprises three stem-loop structures. In some embodiments, the unit structure comprised by the amplification product comprises four stem-loop structures. In some embodiments, the unit structure comprised by the amplification product comprises more than four (e.g., 5, 6, or more) stem-loop structures. In some embodiments, the number of stem-loop structures in the unit structure corresponds to the number of stem-loop structures in the circular probe or circularizable probe or probe set.

In some embodiments, the circular probe or circularizable probe or probe set comprises a double stranded central structure between the stem regions of the first and second stem-loop structures and the double stranded central structure is non-overlapping with the stem regions of the first, second, or third stem-loop structures. In some embodiments, the circular probe or circularizable probe or probe set comprises a first stem-loop structure, a second stem-loop structure, and a third stem-loop structure. In some embodiments, the circular probe or circularizable probe or probe set further comprises a fourth stem-loop structure (e.g., as shown in FIGS. 1A-1B). In some embodiments, a first strand of the double stranded central structure is between the stem regions of the first and second stem-loop structures and a second strand of the double stranded central structure is between the stem regions of the third and fourth stem-loop structures. In some embodiments, a copy of the unit structure in the amplification product is symmetrical. In some embodiments, within one copy of the unit structure in the amplification product, there are complementary sequences that hybridize to form a double stranded region (e.g., double stranded central structure or a stem region). In some embodiments, the sequences that form the double stranded central structure do not overlap with the sequences that form the first, second, third or fourth stem-loop structures.

In some embodiments, the loop region of the first stem-loop structure comprises a sequence that hybridizes to the target nucleic acid (optionally, for ligation of the circularizable probe or probe set using the target nucleic acid as a template), and the loop region of the second, third, and/or fourth stem-loop structure comprises one or more barcode sequences or complements thereof.

In some embodiments, the loop region of the second, third, or fourth stem-loop structure comprises a primer binding sequence for initiating rolling circle amplification. In some embodiments, provided herein is a primer that hybridizes to a circular or circularizable probe or probe set (e.g., to a loop region of a circular or circularizable probe or probe set). In some embodiments, the primer also hybridizes to the target nucleic acid. In some embodiments, a 3' end of the primer hybridizes to the loop region of the circular or circularizable probe or probe set, and a 5' region of the primer hybridizes to the target nucleic acid. In some embodiments, the primer hybridizes to a region of interest comprised by the target nucleic acid. In some embodiments, the region of interest is a single nucleotide (e.g., a SNP). In some embodiments, the region of interest comprises 2, 3, 4, 5, 6, 7, 8, 9, 10, or more nucleotides. In some embodiments, a 5' end and 3' end of the circularizable probe or probe set are ligated to each other using the primer as a template. In some embodiments, stable hybridization of the primer to the circular or circularizable probe or probe set depends on hybridization of the primer to the target nucleic acid (e.g., to the region of interest).

In some embodiments, a circularizable probe provided herein comprises four stem-loop structures and a double-stranded central region. For example, a circularizable probe provided herein can comprise, from 5' to 3', a first portion of loop 1, a first stem 1 sequence, a first sequence of the double stranded central structure, a first stem 2 sequence, a loop 2 sequence, a second stem 2 sequence, a first stem 3 sequence, a loop 3 sequence, a second stem 3 sequence, a second sequence of the double stranded central structure, a first stem 4 sequence, a loop 4 sequence, a second stem 4 sequence, a second stem 1 sequence, and a second portion of loop 1. The first and second sequence of a stem can be reverse complements of each other, so that the first and second sequence of the stem hybridize to each other to form a stem (e.g., the first stem 1 sequence hybridizes to the second stem 1 sequence to form a stem-loop structure, the first stem 2 sequence hybridizes to the second stem 2 sequence to form a stem-loop structure, and so forth). The first sequence and the second sequence of the double stranded central structure can also be reverse complements of each other, such that the circularizable probe forms a structure as shown in FIG. 1A. In some embodiments, the first and second portion of loop 1 hybridize to a sequence of the target nucleic acid such that the 5' end and 3' end are juxtaposed for ligation using the target nucleic acid as a template, with or without gap filling prior to ligation. It will be understood by one of skill in the art that the described structure could be provided as two or more nucleic acid molecules and include additional ligation points. The additional ligation point(s) can be one or more loop regions (e.g., loop regions that hybridize to the target nucleic acid or to a splint), or within one or more stem regions and/or strands of the double stranded central structure (e.g., the ligation can be templated by the other strand of the stem or by the other strand of the double stranded central structure).

In some embodiments, a circularizable probe set provided herein comprises two or more nucleic acid molecules that are ligated together to form a circularized probe. For example, a first nucleic acid molecule can comprise, from 5' to 3' a first portion of loop 1, a first stem 1 sequence, a first sequence of the double stranded central structure, a first stem 2 sequence, and a first portion of loop 2; and a second nucleic acid molecule can comprise, from 5' to 3', a second portion of loop 2, a second stem 2 sequence, a first stem 3 sequence, a loop 3 sequence, a second stem 3 sequence, a second sequence of the double stranded central structure, a first stem 4 sequence, a loop 4 sequence, a second stem 4 sequence, a second stem 1 sequence, and a second portion of loop 1. The first and second sequence of a stem can be reverse complements of each other, so that the first and second sequence of the stem hybridize to each other to form a stem (e.g., the first stem 1 sequence of the first nucleic acid molecule hybridizes to the second stem 1 sequence of the second nucleic acid molecule to form a stem-loop structure, and the first stem 2 sequence of the first nucleic acid molecule hybridizes to the second stem 2 sequence of the second nucleic acid molecule to form a stem-loop structure). Similarly, the first and second stem 3 sequences of the second nucleic acid molecule can hybridize to each other to form a stem-loop structure, and the first and second stem 4 sequences of the second nucleic acid molecule can hybridize to each other to form a stem-loop structure. The first sequence and the second sequence of the double stranded central structure can also be reverse complements of each other, such that the circularizable probe set forms a structure as shown in FIG. 1B. In some embodiments, the first and second portion of loop 1 hybridize to a sequence of the target nucleic acid such that the 5' end of the first nucleic acid molecule and 3' end of the second nucleic acid molecule are juxtaposed for ligation using the target nucleic acid as a template, with or without gap filling prior to ligation. In some embodiments, the first and second portion of loop 2 hybridize to an additional sequence of the target nucleic acid such that the 5' end of the second nucleic acid molecule and the 3' end of the first nucleic acid molecule are juxtaposed for ligation using the target nucleic acid molecule as a template, with or without gap filling prior to ligation.

In some embodiments, a circular or circularizable probe set provided herein comprises one or more stem-loop structures, wherein each stem-loop structure comprises, from 5' to 3' a first stem sequence, a loop sequence, and a second stem sequence, wherein the second stem sequence comprises a reverse complement sequence of the first stem sequence. For example, as shown in FIG. 2D, in an embodiment, a circularizable probe or circularizable probe set provided herein can comprise, from 5' to 3' a first portion of loop 1, a first stem 1 sequence, a central sequence, a first stem 2 sequence, a loop 2 sequence, a second stem 2 sequence, a second stem 1 sequence, and a second portion of loop 1. In another embodiment, a circularizable probe or circularizable probe set provided herein can comprise, from 5' to 3', a first portion of loop 1, a first stem 1 sequence, a first stem 2 sequence, a loop 2 sequence, a second stem 2 sequence, a first stem 3 sequence, a loop 3 sequence, a second stem 3 sequence, and a second portion of loop 1. It will be understood by one of skill in the art that the described structure could be provided as two or more nucleic acid molecules and include additional ligation points. The additional ligation point(s) can be one or more loop regions (e.g., loop regions that hybridize to the target nucleic acid or to a splint), or within one or more stem regions and/or strands of the double stranded central structure (e.g., the ligation can be templated by the other strand of the stem or by the other strand of the double stranded central structure).

In some embodiments, the stem regions of the stem-loop structures disclosed herein (e.g., a first, second, third, and or fourth stem-loop structure) are independently between about 5 and about 20 bp in length. In some embodiments, the stem regions of the stem-loop structures disclosed herein (e.g., a first, second, third, and or fourth stem-loop structure) are independently between about 5 and about 15 bp in length. In some embodiments, the stem regions are independently about 6, about 7, about 8, about 9, or about 10 bp in length. In some embodiments, the stem region of a stem-loop structure is 8 or about 8 bp in length. In some embodiments, the stem region of a stem-loop structure is 9 or about 9 bp in length. In some embodiments, the stem region of a stem-loop structure is 10 or about 10 bp in length. In some embodiments, the stem region of a stem-loop structure can be more than 10 bp in length. In some embodiments, the stem region of a stem-loop structure can be less than 5 bp in length. In some embodiments, the length of the stem regions of two or more stem-loop structures comprised by a unit structure are the same or about the same (e.g., differ by 1, 2, 3, 4, or 5 nucleotides). In some embodiments the lengths of the stem regions of each stem-loop structure in the unit structure are the same or about the same. In some embodiments, the length of a stem region in one stem-loop structure of a unit structure can differ from the length of a stem region of another stem-loop structure in the unit structure, optionally wherein the lengths of the stem regions differ by more than 5 nucleotides or by more than 10 nucleotides.

In some embodiments, the loop regions of the first, second, third, and/or fourth stem-loop structures are independently between about 5 and about 40 nucleotides in length, optionally wherein the loop regions are independently between about 10 and about 20 nucleotides in length. In some embodiments, the loop regions of the first, second, third, and/or fourth stem-loop structures are independently between 5 and 30 nucleotides in length. In some embodiments, the loop regions of the first, second, third, and/or fourth stem-loop structures are independently between 10 and 20 nucleotides in length. In some embodiments, the loop regions of the first, second, third, and/or fourth stem-loop structures are 10, 11, 12, 13, 14, 15, 16, 17, 18, 19, or 10 nucleotides in length. In some embodiments, a loop region of one or more stem-loop structures herein can be more than 30 nucleotides in length. In some embodiments, a loop region of one or more stem-loop structures herein can be shorter than 5 nucleotides in length. In some embodiments, the lengths of the loops in one or more stem-loop structures of the unit structure are the same or about the same (e.g., differ by a length of 1, 2, 3, 4, or 5 nucleotides). In some embodiments, the lengths of each stem-loop structure in the unit structure are the same or about the same (e.g., differ by a length of 1, 2, 3, 4, or 5 nucleotides). In some embodiments, the length of a loop region in one stem-loop structure comprised by the unit structure can differ from the length of a loop region in another stem-loop structure, optionally wherein the lengths of the loops differ by more than 5 nucleotides or more than 10 nucleotides.

In some embodiments, a barcode sequence or complement thereof comprised by a loop region is between or between about 10 and 30 nucleotides in length. In some embodiments, a barcode sequence or complement thereof comprised by a loop region is between or between about 15 and 25 nucleotides in length. In some embodiments, a barcode sequence or complement thereof comprised by a loop region is about 15, 16, 17, 18, 19, 20, 21, 22, 23, 24, or 25 nucleotides in length. In some embodiments, a barcode sequence or complement thereof comprised by a loop region is about 20 nucleotides in length.

In some embodiments, a loop region of the circular probe or circularizable probe or probe set comprises an anchor sequence or complement thereof. In some embodiments, a loop region of the amplification product of the circular probe or circularizable probe set comprises an anchor sequence. In some embodiments, an anchor sequence is a sequence that is common to all probes. In some embodiments, hybridization of a detectably labelled probe to the anchor sequence is used to detect all amplification products of circular or circularizable probes or probe sets in the sample (e.g., to simultaneously light up all analytes in the sample that are associated with a rolling circle amplification product). In some embodiments, an anchor probe is hybridized to the anchor sequence and the anchor probe is immobilized in the sample (e.g., by crosslinking to a matrix). In some embodiments, a sequencing anchor for sequencing-by-ligation (SBL) chemistry is hybridized to an anchor sequence.

In some embodiments, an anchor sequence or complement thereof comprised by a loop region is between or between about 10 and 30 nucleotides in length. In some embodiments, an anchor sequence or complement thereof comprised by a loop region is between or between about 15 and 25 nucleotides in length. In some embodiments, an anchor sequence or complement thereof comprised by a loop region is about 15, 16, 17, 18, 19, 20, 21, 22, 23, 24, or 25 nucleotides in length. In some embodiments, an anchor sequence or complement thereof comprised by a loop region is about 20 nucleotides in length.

In some embodiments, a stem-loop structure herein is a hairpin structure (e.g., a stem and an exterior loop). In some embodiments, a stem-loop structure herein comprises an internal loop. In some embodiments, a stem-loop structure herein comprises an internal bulge. In some embodiments, a stem-loop structure herein comprises multiple loops (e.g., an internal loop and an exterior loop). In some embodiments, a stem-loop structure herein comprises a single loop (e.g., an exterior loop). In some embodiments, a loop region of a stem-loop structure comprises a ligation site (e.g., the loop can be a split loop region that is not connected by a phosphodiester bond until the split loop region is ligated, optionally wherein the ligation circularizes the probe or probe set). In some embodiments, a loop region can comprise a sequence for hybridizing to a target nucleic acid, wherein the target nucleic acid is used as a template for ligation of the probe or probe set. In some embodiments, a loop region can comprise a sequence for hybridization to a splint that is distinct from the probe or target nucleic acid, wherein the splint is used as a template for ligation of the circularizable probe or probe set. The sequence for hybridizing to the target nucleic acid and/or splint can be a split hybridization region (e.g., a region comprised by a 5' end and a 3' end of the circular or circularizable probe or probe set, as shown in FIG. 1A and FIG. 1B). In some embodiments, the split loop region comprises a sequence for hybridizing to the target nucleic acid that is between about 20 and 50 nucleotides in length. In some embodiments, the sequence for hybridizing to the target nucleic acid is between about 30 and 45 nucleotides in length. In some embodiments, the sequence for hybridizing to the target nucleic acid is between about 30 and 40 nucleotides in length.

In some aspects, a circular probe or circularizable probe or probe set comprises a double stranded central region. In some embodiments, the double stranded central structure is between about 5 and about 15 bp in length, optionally wherein the double stranded central structure is about 6, about 7, about 8, about 9, or about 10 bp in length. In some embodiments, the double stranded central structure is between 5 and 15 bp in length. In some embodiments, the double stranded central structure is 8 or about 8 bp in length. In some embodiments, the double stranded central structure is 9 or about 9 bp in length. In some embodiments, the double stranded central structure is 10 or about 10 bp in length. In some embodiments, the double stranded central structure is greater than 10 bp in length.

In some embodiments, a circularizable probe or probe set provided herein is between or between about 30 and 100 nucleotides in length. In some embodiments, a circularizable probe or probe set provided herein is between or between about 100 and 150 nucleotides in length. In some embodiments, a circularizable probe or probe set provided herein is between or between about 150 and 200 nucleotides in length.

In some embodiments, a circularizable probe provided herein is a single nucleic acid molecule. In other embodiments, a circularizable probe set provided herein comprises two, three, four, or more nucleic acid molecules. For example, a circularizable probe set can comprise two nucleic acid molecules that are ligated together to generate the circularized probe. One challenge associated with generating certain circular or circularizable probes or probe sets provided herein is the difficulty of synthesizing long nucleic acid molecules (e.g., the length required for a probe comprising multiple stem-loop structures including loop regions for hybridizing to a target nucleic acid, for hybridization of a primer, and for inclusion of one or more barcode sequences or complements thereof). In some aspects, the use of two or more nucleic acid molecules in a circularizable probe set circumvents challenges related to the synthesis of long nucleic acid molecules. In some embodiments, the two or more nucleic acid molecules can be ligated to each other using the target nucleic acid molecule (e.g., a single target nucleic acid molecule) as a template for the first and the second ligation (e.g., as shown in FIG. 1B). In some embodiments, the two or more nucleic acid molecules can be ligated to each other using a first target nucleic acid molecule as a template for the first ligation and a second target nucleic acid molecule as a template for the second ligation. Thus, in some embodiments, the circularizable probe set can be used in a proximity ligation assay, wherein generating the circularized probe from the circularizable probe set depends on a first and second ligation using first and second target nucleic acid molecules as templates (e.g., generating the circularized probe depends on proximity of the first target nucleic acid molecule and the second target nucleic acid molecule). In other embodiments, a first ligation can be performed using the target nucleic acid molecule as a template (e.g., to detect a sequence of interest in the target nucleic acid), and the second ligation can be performed using any of a splint hybridizing to a loop region of the circularizable probe set, a strand of a stem region, or a strand of the double stranded central region as a template. In some embodiments, generation of a circularized probe from a circularizable probe set provided herein does not require the addition of splints that are distinct from the circularizable probe set and/or target nucleic acid, for example, because the double stranded stem regions and/or double stranded central region can provide a template for ligation of one strand.

In some embodiments, the circular probe or circularizable probe or probe set comprises DNA. In some embodiments, the circular probe or circularizable probe or probe set comprises one or more ribonucleotides, optionally wherein the circular probe or circularizable probe or probe set comprises no more than four consecutive ribonucleotides. In some embodiments, the one or more ribonucleotides are at and/or near a ligatable 3' end, optionally wherein the circularizable probe or probe set comprises a ribonucleotide at a 3' end. In some embodiments, the one or more ribonucleotides are at and/or near a ligatable 3' end comprised by a loop region of the circularizable probe or probe set. In some embodiments, the one or more ribonucleotides are at and/or near a ligatable 3' end comprised by a loop region that hybridizes to a target nucleic acid, optionally wherein the loop region hybridizes to a region of interest comprised by the target nucleic acid. In some embodiments, circularization of a circularizable probe or probe set herein depends on hybridization between a sequence of the loop region and the region of interest comprised by the target nucleic acid (e.g., hybridization of a 3' ligatable end to the region of interest). In some embodiments, the region of interest is a single nucleotide (e.g., a SNP). In some embodiments, the region of interest comprises 2, 3, 4, 5, 6, 7, 8, 9, 10, or more nucleotides. In some embodiments, the method comprises detecting the presence of absence of an amplification product of a circularizable probe or probe set herein, wherein the presence or absence of the amplification product is indicative of a sequence of the region of interest.

In some embodiments, a method provided herein comprises generating the circularized probe from the circularizable probe or probe set. In some embodiments, the generating comprises ligating a 5' end sequence and a 3' end sequence of the circularizable probe or probe set. In some embodiments, the generating comprises ligating two or more nucleic acid molecules of the circularizable probe set. In some embodiments, the generating comprises ligating a 5' end sequence of a first nucleic acid molecule to a 3' end sequence of a second nucleic acid molecule, and ligating the 5' end sequence of the second nucleic acid molecule to the 3' end sequence of the first nucleic acid molecule, thereby generating the circularized probe. In some embodiments, the 5' end sequence and the 3' end sequence are in the loop region of the first, second, third, or fourth stem-loop structure. In some embodiments, the 5' end sequence and the 3' end sequence are hybridized to the target nucleic acid, optionally wherein the 5' end sequence and the 3' end sequence are ligated using the target nucleic acid as a template. In some embodiments, the target nucleic acid is a ribonucleic acid (e.g., mRNA) and the 3' end sequence comprises one or more ribonucleotides. In some embodiments, the 5' end sequence and the 3' end sequence are hybridized to a splint that is distinct from the circularizable probe or probe set and the target nucleic acid, optionally wherein the 5' end sequence and the 3' end sequence are ligated using the splint as a template, and optionally wherein the splint comprises a sequence that hybridizes to the target nucleic acid. In some embodiments, hybridization of the splint to the target nucleic acid stabilizes hybridization of the splint and/or circularizable probe or probe set. In some embodiments, the 5' end sequence and the 3' end sequence are in a strand of the stem region of the first, second, third, or fourth stem-loop structure, optionally wherein the 5' end sequence and the 3' end sequence are ligated using the other strand of the stem region as a template. In some embodiments, the 5' end sequence and the 3' end sequence are in a strand of the double stranded central structure, optionally wherein the 5' end sequence and the 3' end sequence are ligated using the other strand of the double stranded central structure as a template.

In some embodiments, a method provided herein comprises generating the circularized probe from a circularizable probe and a 5' end sequence and a 3' end sequence of the circularizable probe is ligated. In some embodiments, wherein the generating comprises a first ligation and a second ligation (e.g., generating a circularized probe from a circularizable probe set comprising two or more nucleic acid molecules), the first ligation and the second ligation are performed using the target nucleic acid as a template for ligation. In some embodiments, the first ligation is performed using the target nucleic acid as a template for ligation, and the second ligation is performed using a strand of a stem region of the circularizable probe set as a template, or using a splint that is distinct from the circularizable probe or probe set and the target nucleic acid. In some embodiments, the first nucleic acid molecule and second nucleic acid molecule of the circularizable probe set are hybridized to each other prior to hybridizing the circularizable probe set to the target nucleic acid.

In some embodiments, the amplification product comprises one or more barcode sequences or complements thereof (e.g., a sequence complementary to the sequence comprised by the circular or circularized probe). In some embodiments, one or more loop regions of the circular probe or circularizable probe or probe set comprise one or more barcode sequences or complements thereof for detection of the amplification product (e.g., as described in Section II). In some embodiments, the one or more barcode sequences or complements thereof correspond to the target nucleic acid or a portion thereof. In some embodiments, the one or more barcode sequences are comprised by one or more loop regions of the amplification product. In some embodiments, at least two loop regions of the amplification product comprise barcode sequences. In some embodiments, the same barcode sequence is comprised by two loop regions of the amplification product. In some embodiments, different barcode sequences are comprised by two loop regions of the amplification product. In some embodiments, a barcode region of a circularizable probe or probe set herein is a split barcode region (e.g., a barcode sequence comprised by a 5' end and a 3' end of the circularizable probe or probe set, wherein the 5' end and 3' end are not directly connected by a phosphodiester bond prior to ligation). In some embodiments, the split barcode sequence is ligated (e.g., using a primer or other splint as a template).

In some embodiments, the circular probe or circularizable probe or probe set comprises at least two stem-loop structures, and the first stem-loop structure comprises a barcode sequence(s) or complements thereof and the second stem-loop structure comprises a sequence for hybridizing to the target nucleic acid. In some embodiments, the circular probe or circularizable probe or probe set comprises at least three stem-loop structures, and the first stem-loop structure comprises a primer binding sequence for initiating rolling circle amplification, the second stem-loop structure comprises a barcode sequence(s) or complements thereof, the third stem-loop structure comprises a sequence for hybridizing to the target nucleic acid. In some embodiments, the circular probe or circularizable probe or probe set comprises at least four stem-loop structures, and the first stem-loop structure comprises a primer binding sequence for initiating rolling circle amplification, the second stem-loop structure comprises a barcode sequence(s) or complements thereof, the third stem-loop structure comprises an anchor binding sequence, and the fourth stem-loop structure comprises a sequence for hybridizing to the target nucleic acid.

IV. Ligation and Rolling Circle Amplification

In some embodiments, the circularized probe is generated using enzymatic ligation and/or chemical ligation. In some embodiments, the circularized probe is generated using template dependent ligation and/or template independent ligation. In some embodiments, the circularized probe is generated using a ligase having an RNA-templated DNA ligase activity and/or an RNA-templated RNA ligase activity. In some embodiments, the circularized probe is generated using a ligase selected from the group consisting of a Chlorella virus DNA ligase (PBCV DNA ligase), a T4 RNA ligase, a T4 DNA ligase, and a single-stranded DNA (ssDNA) ligase. In some embodiments, the circularized probe is generated using a PBCV-1 DNA ligase or variant or derivative thereof and/or a T4 RNA ligase 2 (T4 Rnl2) or variant or derivative thereof.

In some embodiments, the amplification product of a circular or circularizable probe or probe set provided herein comprises nucleic acids. In some embodiments, the amplification product is a rolling circle amplification product generated using the circularized probe described in Section III as template. In some embodiments, the amplification product is a rolling circle amplification product comprising a plurality of sequences that are complementary to sequences comprised by the circularized probe. In some embodiments, the amplification product contains natural and unnatural nucleotides. For example, the amplification product may comprise modified nucleotides, non-nucleotides, or synthetic nucleotides. Nucleotides amendable to the present application include the natural nucleotides of DNA (deoxyribonucleic acid), including adenine (A), guanine (G), cytosine (C), and thymine (T), and the natural nucleotides of RNA (ribonucleic acid), adenine (A), uracil (U), guanine (G), and cytosine (C). Additional suitable bases include natural bases, such as deoxyadenosine, deoxythymidine, deoxyguanosine, deoxycytidine, inosine, diamino purine; base analogs, such as 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, 0(6)-methylguanine, 4-((3-(2-(2-(3-aminopropoxy)ethoxy)ethoxy)propyl)amino)pyrimidin-2(1H)-one, 4-amino-5-(hepta-1,5-diyn-1-yl)pyrimidin-2(1H)-one, 6-methyl-3,7-dihydro-2H-pyrrolo[2,3-d]pyrimidin-2-one, 3H-benzo[b]pyrimido[4,5-e][1,4]oxazin-2(10H)-one, and 2-thiocytidine; modified nucleotides, such as 2'-substituted nucleotides, including 2'-O-methylated bases and 2'-fluoro bases; and modified sugars, such as 2'-fluororibose, ribose, 2'-deoxyribose, arabinose, and hexose; and/or modified phosphate groups, such as phosphorothioates and 5'-N-phosphoramidite linkages. In some embodiments, the modified nucleotides are amine-modified nucleotides.

In some embodiments, the amplification product is between about 1 and about 85 kilobases in length, such as between any of about 1 and about 15 kilobases, about 10 and about 30 kilobases, about 20 and about 40 kilobases, about 30 and about 50 kilobases, about 40 and about 60 kilobases, about 50 and about 70 kilobases, and about 60 and about 85 kilobases in length. In some embodiments, the amplification product is at least 1 kilobase in length, such as any of about 15, 25, 35, 45, 55, 65, or 85 kilobases in length. In some embodiments, the amplification product is more than 85 kilobases in length.

In some embodiments, the amplification product is a rolling circle amplification product comprising a barcode sequence (e.g., as described in Section II or III) or complement thereof corresponding to an analyte in the biological sample, and the nucleic acid concatemer is between about 1 and about 15 kilobases, between about 15 and about 25 kilobases, between about 25 and about 35 kilobases, between about 35 and about 45 kilobases, between about 45 and about 55 kilobases, between about 55 and about 65 kilobases, between about 65 and about 75 kilobases, or more than 75 kilobases in length.

In some embodiments, the amplification product comprises between about 10 and about 100, between about 100 and about 1,000, between about 1,000 and about 5,000, between about 5,000 and about 10,000, or more than 10,000 copies of the unit structure. In some embodiments, the amplification product comprises between 10 and 100, between 100 and 1,000, between 1,000 and 5,000, between 5,000 and 10,000, or more than 10,000 copies of the unit structure. In some embodiments, the amplification product comprises between or between about 50 and 100 copies of the unit structure. In some embodiments, the amplification product comprises between or between about 100 and 200 copies of the unit structure. In some embodiments, the amplification product comprises between or between about 200 and 500 copies of the unit structure. In some embodiments, the amplification product comprises between or between about 500 and 1000 copies of the unit structure.

In some embodiments, steric hindrance between the multiple copies of the unit structure promotes compacting the amplification product in situ in the biological sample or in a matrix embedding the biological sample or molecules thereof.

In some embodiments, the unit structure comprises stem-loop and double stranded central structures that facilitate stacking of the multiple copies of the unit structure, thereby stabilizing and/or compacting the amplification product in situ in the biological sample or in a matrix embedding the biological sample or molecules thereof. In some embodiments, the stacking comprises rotation of the unit structures relative to a linker sequence, such that the amplification product comprises a stack of unit structures connected by linkers. In some embodiments, the linker comprises a sequence of the loop region comprising the primer binding site.

In some embodiments, the unit structure comprises stem-loop and double stranded central structures that facilitate generation of a multi-unit structure comprising multiple copies of the unit structure around a central vertex, thereby stabilizing and/or compacting the amplification product in situ in the biological sample or in a matrix embedding the biological sample or molecules thereof. In some embodiments, the vertex comprises a sequence complementary to the primer binding sequence for initiating rolling circle amplification. In some embodiments, the vertex comprises a sequence complementary to the loop region used as a template at the origin of replication (e.g., initiating rolling circle amplification). In some embodiments, the multi-unit structure comprises 3, 4, or 5 copies of the unit structure around a central vertex (e.g., in some embodiments the multi-unit structure comprises 4 copies of the unit structure, as shown in FIG. 3). In some embodiments, steric hindrance between the multiple copies of the unit structure facilitates stacking of multiple copies of the multi-unit structure, thereby stabilizing and/or compacting the amplification product in situ in the biological sample or in a matrix embedding the biological sample or molecules thereof (e.g., as shown in FIG. 3).

In some embodiments, the amplification product comprises multiple copies of the unit structure, wherein one or more loop regions comprising barcode sequences or complements thereof are oriented toward the outside of a structure formed by the amplification product. In some embodiments, the amplification product comprises a stack of multi-unit structures, wherein each multi-unit structure comprises multiple unit structures. In some embodiments, the stack of multi-unit structures comprises loop regions comprising one or more barcode sequences oriented toward the outside of the stack. In some aspects, barcode sequences or complements thereof that are oriented toward the outside of a structure formed by the amplification product provide certain advantages during detection (e.g., availability of a barcode sequence or complement thereof for binding labelled probes (e.g., detection oligos)).

In some embodiments, the amplification product forms a nanoball such as one having a diameter between about 0.1 µm and about 3 µm. In some embodiments, the nanoball has a diameter of between about 0.1 µm and about 4 µm, such as between any of about 0.1 µm and about 0.5 µm, about 0.2 µm and about 2 µm, about 1 µm and about 3 µm, and about 2 µm and about 4 µm. In some embodiments, the nanoball diameter is at least about 0.1 µm, such as at least any of about 0.2 µm, 0.5 µm, 1 µm, 1.5 µm, 2 µm, 2.5 µm, 3 µm, 3.5 µm, and 4 µm. In some embodiments, the amplification product forms a nanoball comprising multiple copies of a unit structure.

In some embodiments, the method comprises comprising crosslinking the amplification product to itself, to one or more other molecules in the biological sample, and/or to a matrix embedding the biological sample or molecules thereof, optionally wherein the crosslinking reduces the mobility of the amplification product in the biological sample and/or in the matrix. In some embodiments, crosslinking the amplification product (e.g., crosslinking the amplification product to itself) can increase the stability of the unit structures. In some embodiments, crosslinking the amplification product stabilizes the compacted structure of the amplification product (e.g., a multi-unit structure comprising multiple copies of the unit structure around a central vertex, and/or a stack comprising multiple copies of the unit structure). In some embodiments, crosslinking the amplification product stabilizes the position of the amplification product in the sample.

In some aspects, the target nucleic acid, circular or circularizable probe or probe set, and/or amplification product generated from the circular or circularizable probe or probe set can be anchored to a polymer matrix (e.g., by crosslinking). For example, the polymer matrix can be a hydrogel. In some embodiments, one or more of the circular or circularizable probes or probe sets, or a primer or anchor probe can be modified to contain functional groups (e.g., an acrydite or photoreactive nucleotides) that can be used as an anchoring site to attach the probe(s) and/or amplification product to a polymer matrix. In some embodiments, the amplification product can comprise one or more amine-modified nucleotides. Exemplary polymer matrices that can be employed in accordance with the provided embodiments comprise those described in, for example, US 2016/0024555, US 2018/0251833, US 2016/0024555, US 2018/0251833 and US 2017/0219465. In some examples, the scaffold can comprise oligonucleotides (e.g., target nucleic acids), polymers or chemical groups, to provide a matrix and/or support structures. Exemplary methods of anchoring molecules such as an amplification product to a polymer matrix are described in Section II A (iv. Embedding).

In some embodiments, a probe disclosed herein is amplified through rolling circle amplification (RCA). In some embodiments, the method comprises using a circular or circularizable construct hybridized to the nucleic acid of interest to generate a circular nucleic acid. In some embodiments, the RCA comprises a linear RCA. In some embodiments, the RCA comprises a branched RCA. In some embodiments, the RCA comprises a dendritic RCA. In some embodiments, the RCA comprises any combination of the foregoing. In some embodiments, the circular nucleic acid is a construct formed using ligation. In some embodiments, the circular construct is formed using template primer extension followed by ligation. In some embodiments, the circular construct is formed by providing an insert between ends to be ligated. In some embodiments, the circular construct is formed using a combination of any of the foregoing. In some embodiments, the ligation is a DNA-DNA templated ligation. In some embodiments, the ligation is an RNA-RNA templated ligation. Exemplary RNA-templated ligation probes and methods are described in US 2020/0224244 which is incorporated herein by reference in its entirety. In some embodiments, the ligation is a RNA-DNA templated ligation. In some embodiments, a splint is provided as a template for ligation.

In some embodiments, the circular probe or circularizable probe or probe set comprises one or more ribonucleotides, optionally wherein the circular probe or circularizable probe or probe set comprises no more than four consecutive ribonucleotides. In some embodiments, the one or more ribonucleotides are at and/or near a ligatable 3' end, optionally wherein the circularizable probe or probe set comprises a ribonucleotide at a 3' end. In some embodiments, the one or more ribonucleotides are at and/or near a ligatable 3' end comprised by a loop region of the circularizable probe or probe set. In some embodiments, the one or more ribonucleotides are at and/or near a ligatable 3' end comprised by a loop region that hybridizes to a target nucleic acid (e.g., target RNA), optionally wherein the loop region hybridizes to a region of interest comprised by the target nucleic acid.

In some embodiments, a probe disclosed herein (e.g., a circularizable probe or probe set) can comprise a 5' flap which may be recognized by a structure-specific cleavage enzyme, e.g. an enzyme capable of recognizing the junction between single-stranded 5' overhang and a DNA duplex, and cleaving the single-stranded overhang. It will be understood that the branched three-strand structure which is the substrate for the structure-specific cleavage enzyme may be formed by 5' end of one probe part and the 3' end of another probe part when both have hybridized to the target nucleic acid molecule, as well as by the 5' and 3' ends of a one-part probe. Enzymes suitable for such cleavage include Flap endonucleases (FENS), which are a class of enzymes having endonucleolytic activity and being capable of catalyzing the hydrolytic cleavage of the phosphodiester bond at the junction of single- and double-stranded DNA. Thus, in some embodiment, cleavage of the additional sequence 5' to the first target-specific binding site is performed by a structure-specific cleavage enzyme, e.g. a Flap endonuclease. Suitable Flap endonucleases are described in Ma et al. 2000. *JBC* 275, 24693-24700 and in US 2020/0224244 and may include *P. furiosus* (Pfu), *A. fulgidus* (Afu), *M. jannaschii* (Mja) or *M. thermoautotrophicum* (Mth). In other embodiments an enzyme capable of recognizing and degrading a single-stranded oligonucleotide having a free 5' end may be used to cleave an additional sequence (5' flap) from a structure as described above. Thus, an enzyme having 5' nuclease activity may be used to cleave a 5' additional sequence. Such 5' nuclease activity may be 5' exonuclease and/or 5' endonuclease activity. A 5' nuclease enzyme is capable of recognizing a free 5' end of a single-stranded oligonucleotide and degrading said single-stranded oligonucleotide. A 5' exonuclease degrades a single-stranded oligonucleotide having a free 5' end by degrading the oligonucleotide into constituent mononucleotides from its 5' end. A 5' endonuclease activity may cleave the 5' flap sequence internally at one or more nucleotides. Further, a 5' nuclease activity may take place by the enzyme traversing the single-stranded oligonucleotide to a region of duplex once it has recognized the free 5' end, and cleaving the single-stranded region into larger constituent nucleotides (e.g. dinucleotides or trinucleotides), or cleaving the entire 5' single-stranded region, e.g. as described in Lyamichev et al. 1999. *PNAS* 96, 6143-6148 for Taq DNA polymerase and the 5' nuclease thereof. Preferred enzymes having 5' nuclease activity include Exonuclease VIII, or a native or recombinant DNA polymerase enzyme from *Thermus aquaticus* (Taq), *Thermus thermophilus* or *Thermus flavus*, or the nuclease domain therefrom.

Following formation of the circular nucleic acid, in some instances, an amplification primer is added. In other instances, the amplification primer is added with circular or circularizable probe(s) or probe set(s). In some instances, the amplification primer may be complementary to the circular or circularizable probe or probe set, and the amplification primer may additionally comprise a sequence that is complementary to a sequence in the target nucleic acid. In some embodiments, a washing step is performed to remove any unbound probes, primers, etc. In some embodiments, the wash is a stringency wash. Washing steps can be performed at any point during the process to remove non-specifically bound probes, probes that have ligated, etc.

In some instances, upon addition of a DNA polymerase in the presence of appropriate dNTP precursors and other cofactors, the amplification primer is elongated by replication of multiple copies of the template. The amplification step can utilize isothermal amplification or non-isothermal amplification. In some embodiments, after the formation of the hybridization complex and any subsequent circularization (such as ligation of, e.g., a circularizable probe or probe set) the circular probe is rolling-circle amplified to generate a RCA product (e.g., amplicon) containing multiple copies of the circular.

Suitable examples of DNA polymerases that can be used include, but are not limited to: E. coli DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

In some embodiments, rolling circle amplification products are generated using a polymerase selected from the group consisting of Phi29 DNA polymerase, Phi29-like DNA polymerase, M2 DNA polymerase, B103 DNA polymerase, GA-1 DNA polymerase, phi-PRD1 polymerase, Vent DNA polymerase, Deep Vent DNA polymerase, Vent (exo−) DNA polymerase, KlenTaq DNA polymerase, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, and a variant or derivative thereof.

Following amplification, the sequence of the amplicon (e.g., RCA product) or a portion thereof, is determined or otherwise analyzed, for example by using detectably labeled probes and imaging. The sequencing or analysis of the amplification products can comprise sequencing by hybridization, sequencing by ligation, and/or fluorescent in situ sequencing, and/or wherein the in situ hybridization comprises sequential fluorescent in situ hybridization. In some instances, a sequence of the RCA product is detected using, e.g., the secondary and higher order probes and detection oligonucleotides described herein.

In some embodiments, a circularizable probe or probe set contains one or more barcodes. In some embodiments, the barcodes are bound by detectable probes, which may but do not need to be detectably labeled. In some embodiments, one or more decoding schemes are used to decode the signals, such as fluorescence, for sequence determination. Exemplary decoding schemes are described in Eng et al., "Transcriptome-scale Super-Resolved Imaging in Tissues by RNA SeqFISH+," Nature 568(7751):235-239 (2019); Chen et al., "Spatially resolved, highly multiplexed RNA profiling in single cells," Science; 348(6233):aaa6090 (2015); U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

V. Detection and Analysis

In some aspects, the provided methods involve analyzing, e.g., detecting or determining, one or more sequences present in the target nucleic acid and in an amplification product of a circular or circularized probe described herein (e.g., one or more sequences of one or more loop regions in the amplification product). In some embodiments, the detecting comprises hybridizing one or more detectably labeled probes to the amplification product (e.g., to a loop region of the amplification product). In some embodiments, the detecting comprises hybridization of one or more detectably labeled probes to adaptor probes that hybridize to the amplification product. In some embodiments, the one or more detectably labeled probes or adapter probes hybridize to one or more loop regions comprised by the unit structure of the amplification product. In some embodiments, the analysis comprises determining the sequence of all or a portion of the amplification product (e.g., a barcode sequence or a complement thereof, optionally wherein the sequence is a sequence of a loop region), wherein the sequence is indicative of, associated with, or corresponds to a sequence of the target nucleic acid.

In some embodiments, detection of the amplification product comprises detection of a sequence in a loop region of a stem-loop structure in the amplification product, optionally wherein the sequence in the loop region is a barcode sequence. In some embodiments, the detection of the amplification product comprises contacting the biological sample with one or more detectably-labeled probes that directly or indirectly hybridize to one or more loop regions of the amplification product.

In some cases, analysis is performed on one or more images captured, and may comprise processing the image(s) and/or quantifying signals observed. In some embodiments, images of signals from different fluorescent channels and/or detectable probe hybridization cycles can be compared and analyzed. In some embodiments, images of signals (or absence thereof) at a particular location in a sample from different fluorescent channels and/or sequential detectable probe hybridization cycles can be aligned to analyze an analyte at the location. For instance, a particular location in a sample can be tracked and signal spots from sequential probe hybridization (and optionally ligation) cycles can be analyzed to detect a target polynucleotide sequence (e.g., a barcode sequence or subsequence thereof) in a nucleic acid at the location. The analysis may comprise processing information of one or more cell types, one or more types of analytes, a number or level of analyte, and/or a number or level of cells detected in a particular region of the sample. In some embodiments, the analysis comprises detecting a sequence e.g., a barcode sequence present in an amplification product at a location in the sample. In some embodiments, the analysis includes quantification of puncta (e.g., if amplification products are detected). In some cases, the analysis includes determining whether particular cells and/or signals are present that correlate with one or more analytes from a particular panel. In some embodiments, the obtained information may be compared to a positive and negative control, or to a threshold of a feature to determine if the sample exhibits a certain feature or phenotype. In some cases, the information may comprise signals from a cell, a region, and/or comprise readouts from multiple detectable labels. In some case, the analysis further includes displaying the information from the analysis or detection step. In some embodiments, software may be used to automate the processing, analysis, and/or display of data.

Methods for binding and identifying a target nucleic acid that uses various probes or oligonucleotides have been described in, e.g., US2003/0013091, US2007/0166708, US2010/0015607, US2010/0261026, US2010/0262374, US2010/0112710, US2010/0047924, and US2014/0371088, each of which is incorporated herein by reference in its entirety. Detectably-labeled probes can be useful for detecting multiple target nucleic acids and be detected in one or more hybridization cycles (e.g., sequential hybridization in a FISH-type assay, sequencing by hybridization).

In some embodiments, the methods comprise determining the sequence of all or a portion of the amplification product, such as one or more barcode sequences present in the amplification product. In some embodiments, the amplification product is a nucleic acid concatemer. In some embodiments, the sequence of the amplification product or barcode thereof, is indicative of a sequence of the target nucleic acid to which the amplification product is hybridized. In some embodiments, the analysis and/or sequence determination comprises sequencing all or a portion of the amplification product and/or in situ hybridization to the amplification product. In some embodiments, the sequencing step involves sequencing by hybridization, sequencing by ligation, sequencing by synthesis, sequencing by binding, and/or fluorescent in situ sequencing (FISSEQ), hybridization-based in situ sequencing and/or wherein the in situ hybridization comprises sequential fluorescent in situ hybridization. In some embodiments, the analysis and/or sequence determination comprises detecting a polymer generated by a hybridization chain reaction (HCR) reaction, see e.g., US2017/0009278, which is incorporated herein by reference, for exemplary probes and HCR reaction components. In some embodiments, the detection or determination comprises hybridizing to the first overhang a detection oligonucleotide labeled with a fluorophore, an isotope, a mass tag, or a combination thereof. In some embodiments, the detection or determination comprises imaging the probe hybridized to the target nucleic acid (e.g., imaging one or more detectably labeled probes hybridized thereto). In some embodiments, the target nucleic acid is an mRNA in a tissue sample, and the detection or determination is performed when the target nucleic acid and/or the amplification product is in situ in the tissue sample. In some embodiments, the target nucleic acid is an amplification product (e.g., a rolling circle amplification product/nucleic acid concatemer).

In some embodiments, nucleic acid sequence determination (e.g., of a barcode sequence in the RCP of a circular or circularizable probe or probe set disclosed herein) can be carried out using a method that comprises signal amplification. Exemplary signal amplification methods include targeted deposition of detectable reactive molecules around the site of probe hybridization, targeted assembly of branched structures (e.g., bDNA or branched assay using locked nucleic acid (LNA)), hybridization chain reaction (HCR), linear oligonucleotide hybridization chain reaction (LO-HCR), programmed in situ growth of concatemers by enzymatic rolling circle amplification (RCA) (e.g., as described in US 2019/0055594 incorporated herein by reference), hybridization chain reaction, assembly of topologically catenated DNA structures using serial rounds of chemical ligation (clampFISH), signal amplification via hairpin-mediated concatemerization (e.g., as described in US 2019/0106733 and US 2020/0362398 incorporated herein by reference), e.g., primer exchange reactions such as signal amplification by exchange reaction (SABER) or SABER with DNA-Exchange (Exchange-SABER). In some embodiments, a non-enzymatic signal amplification method may be used.

In some embodiments, the assembly for branched signal amplification can comprises an amplifier hybridized directly or indirectly (via one or more oligonucleotides) to a sequence of the target nucleic acid or a probe or probe product. In some embodiments, the assembly includes one or more amplifiers each including an amplifier repeating sequence. In some aspects, the one or more amplifiers is labeled. For exemplary branched signal amplification, see e.g., U.S. Pat. Pub. No. US20200399689A1, US20220064697A1, and Xia et al., Multiplexed Detection of RNA using MERFISH and branched DNA amplification. Scientific Reports (2019), each of which is fully incorporated by reference herein.

HCR is an enzyme-free nucleic acid amplification based on a triggered chain of hybridization of nucleic acid molecules starting from HCR monomers, which hybridize to one another to form a nicked nucleic acid polymer. This polymer is the product of the HCR reaction which is ultimately detected in order to indicate the presence of the target analyte. HCR is described in detail in Dirks and Pierce, 2004, PNAS, 101(43), 15275-15278 and in U.S. Pat. Nos. 7,632,641 and 7,721,721 (see also US 2006/00234261; Chemeris et al, 2008 Doklady Biochemistry and Biophysics, 419, 53-55; Niu et al, 2010, 46, 3089-3091; Choi et al, 2010, Nat. Biotechnol. 28(11), 1208-1212; and Song et al, 2012, Analyst, 137, 1396-1401). HCR monomers typically comprise a hairpin, or other metastable nucleic acid structure. In some embodiments, similar to HCR reactions that use hairpin monomers, LO-HCR can be used for signal amplification. Exemplary methods and compositions for LO-HCR are described in US 2021/0198723, incorporated herein by reference in its entirety.

In some aspects, the provided methods comprise imaging the probe hybridized to the amplification product (e.g., hybridized to a loop region of the amplification product), for example, via binding of the secondary probe (e.g., a detection probe) and detecting the detectable label. In some embodiments, the detection probe comprises a detectable label that can be measured and quantitated. The terms "label" and "detectable label" comprise a directly or indirectly detectable moiety that is associated with (e.g., conjugated to) a molecule to be detected, e.g., a secondary probe that is a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

The term "fluorophore" comprises a substance or a portion thereof that is capable of exhibiting fluorescence in the detectable range. Particular examples of labels that may be used in accordance with the provided embodiments comprise, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenical acetyl transferase, and urease.

Fluorescence detection in tissue samples can often be hindered by the presence of strong background fluorescence. "Autofluorescence" is the general term used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (MaxVision Biosciences), and/or a very intense black dye (e.g., Sudan Black, or comparable dark chromophore).

In some embodiments, a detectable probe containing a detectable label can be used to detect one or more amplification product(s) described herein. In some embodiments, the methods involve incubating the detectable probe containing the detectable label with the sample, washing unbound detectable probe, and detecting the label, e.g., by imaging. In some embodiments, the amplification product(s) remain crosslinked to the target nucleic acid during the washing and detecting steps.

Examples of detectable labels comprise but are not limited to various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as $^{125}$I, $^{35}$S, $^{14}$C, or $^{3}$H. Identifiable markers are commercially available from a variety of sources.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). In some embodiments, exemplary techniques and methods methodologies applicable to the provided embodiments comprise those described in, for example, U.S. Pat. Nos. 4,757,141, 5,151,507 and 5,091,519. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes). Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264. As used herein, the term "fluorescent label" comprises a signaling moiety that conveys information through the fluorescent absorption and/or emission properties of one or more molecules. Exemplary fluorescent properties comprise fluorescence intensity, fluorescence lifetime, emission spectrum characteristics and energy transfer.

Examples of commercially available fluorescent nucleotide analogues readily incorporated into nucleotide and/or polynucleotide sequences comprise, but are not limited to, Cy3-dCTP, Cy3-dUTP, Cy5-dCTP, Cy5-dUTP (Amersham Biosciences, Piscataway, NJ), fluorescein-!2-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, OR). Methods are for custom synthesis of nucleotides having other fluorophores (See, Henegariu et al. (2000) Nature Biotechnol. 18:345).

Other fluorophores available for post-synthetic attachment comprise, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, OR), Cy2, Cy3.5, Cy5.5, and Cy7 (Amersham Biosciences, Piscataway, NJ). FRET tandem fluorophores may also be used, comprising, but not limited to, PerCP-Cy5.5, PE-Cy5, PE-Cy5.5, PE-Cy7, PE-Texas Red, APC-Cy7, PE-Alexa dyes (610, 647, 680), and APC-Alexa dyes.

In some cases, metallic silver or gold particles may be used to enhance signal from fluorescently labeled nucleotide and/or polynucleotide sequences (Lakowicz et al. (2003) Bio Techniques 34:62).

Biotin, or a derivative thereof, may also be used as a label on a nucleotide and/or a polynucleotide sequence, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. As used herein, the term antibody refers to an antibody molecule of any class, or any sub-fragment thereof, such as an Fab.

Other suitable labels for a polynucleotide sequence may comprise fluorescein (FAM), digoxigenin, dinitrophenol (DNP), dansyl, biotin, bromodeoxyuridine (BrdU), hexahistidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

In some embodiments, a nucleotide and/or an oligonucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, and PCT publication WO 91/17160. Many different hapten-capture agent pairs are available for use. Exemplary haptens comprise, but are not limited to, biotin, des-biotin and other derivatives, dinitrophenol, dansyl, fluorescein, Cy5, and digoxigenin. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In some aspects, the detecting involves using detection methods such as flow cytometry; sequencing; probe binding and electrochemical detection; pH alteration; catalysis induced by enzymes bound to DNA tags; quantum entanglement; Raman spectroscopy; terahertz wave technology; and/or scanning electron microscopy. In some aspects, the flow cytometry is mass cytometry or fluorescence-activated flow cytometry. In some aspects, the detecting comprises performing microscopy, scanning mass spectrometry or other imaging techniques described herein. In such aspects, the detecting comprises determining a signal, e.g., a fluorescent signal.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (i.e., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, sequencing can be performed in situ. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) *Anal. Biochem.* 320, 55-65, and Lee et al., (2014)

Science, 343(6177), 1360-1363. In addition, examples of methods and systems for performing in situ sequencing are described in US 2016/0024555, US 2019/0194709, and in U.S. Pat. Nos. 10,138,509, 10,494,662 and 10,179,932. Exemplary techniques for in situ sequencing comprise, but are not limited to, STARmap (described for example in Wang et al., (2018) Science, 361(6499) 5691), MERFISH (described for example in Moffitt, (2016) Methods in Enzymology, 572, 1-49), hybridization-based in situ sequencing (HybISS) (described for example in Gyllborg et al., Nucleic Acids Res (2020) 48(19):e112, and FISSEQ (described for example in US 2019/0032121).

In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, US 2011/0059865, US 2005/0100900, U.S. Pat. No. 9,217,178, US 2009/0118128, US 2012/0270305, US 2013/0260372, and US 2013/0079232.

In some embodiments, sequence analysis of nucleic acids (e.g., nucleic acids such as probes or RCA products comprising barcode sequences) can be performed by sequential hybridization (e.g., sequencing by hybridization and/or sequential in situ fluorescence hybridization). Sequential fluorescence hybridization can involve sequential hybridization of detectable probes comprising an oligonucleotide and a detectable label. In some embodiments, a method disclosed herein comprises sequential hybridization of the detectable probes disclosed herein, including detectably labeled probes (e.g., fluorophore conjugated oligonucleotides) and/or probes that are not detectably labeled per se but are capable of binding (e.g., via nucleic acid hybridization) and being detected by detectably labeled probes. Exemplary methods comprising sequential fluorescence hybridization of detectable probes are described in US 2019/0161796, US 2020/0224244, US 2022/0010358, US 2021/0340618, and WO 2021/138676, all of which are incorporated herein by reference. In some embodiments, the methods provided herein can include analyzing the identifier sequences (e.g., analyte sequences or barcode sequences) by sequential hybridization and detection with a plurality of labeled probes (e.g., detection oligonucleotides).

In some embodiments, provided herein are methods for in situ analysis of analytes in a sample using sequential probe hybridization. In some aspects provided herein is a method for analyzing a biological sample, comprising: a) generating a rolling circle amplification product (RCP) of a circular or circularizable probe or probe set described herein (e.g., in Section III, such as a self-compacting circularizable probe or probe set comprising a first stem-loop structure, a second stem-loop structure, a third stem-loop structure, a fourth stem-loop structure, and a double stranded central structure), the RCP comprising an identifier sequence such as a barcode sequence or analyte sequence, wherein the identifier sequence is associated with an analyte of interest and is assigned a signal code sequence; b) contacting the biological sample with a first probe (e.g., an intermediate probe such as an L-probe) and a first detectably labeled probe to generate a first complex comprising the first probe hybridized to the RCP and the first detectably labeled probe hybridized to the first probe, wherein the first probe comprises (i) a recognition sequence (e.g., a target-binding sequence) complementary to the identifier sequence (e.g., barcode sequence or analyte sequence) and (ii) a first landing sequence (e.g., an overhang sequence), and wherein the first detectably labeled probe comprises a sequence complementary to the first landing sequence; c) detecting a first signal associated with the first detectably labeled probe, wherein the first signal corresponds to a first signal code in the signal code sequence; d) contacting the biological sample with a second probe (e.g., an intermediate probe such as L-probe) and a second detectably labeled probe to generate a second complex comprising the second probe hybridized to the RCP and the second detectably labeled probe hybridized to the second probe, wherein the second probe comprises (i) a recognition sequence (e.g., a target-binding sequence) complementary to the identifier sequence (e.g., barcode sequence or analyte sequence) and (ii) a second landing sequence (e.g., an overhang sequence), and wherein the second detectably labeled probe comprises a sequence complementary to the second landing sequence; and e) detecting a second signal associated with the second detectably labeled probe, wherein the second signal corresponds to a second signal code in the signal code sequence, wherein the signal code sequence comprising the first signal code and the second signal code is determined at a location in the biological sample, thereby decoding the identifier sequence (e.g., barcode sequence or analyte sequence) and identifying the analyte of interest at the location in the biological sample. In some embodiments, the detectable label of the first detectably labeled probe and the detectable label of the second detectably labeled probe are the same. In some embodiments, the detectable labels of the first detectably labeled probe and the second detectably labeled probe are different. In some embodiments, the first signal code and the second signal code are the same. In some embodiments, the first signal code and the second signal code are different.

In some embodiments, the first probe (e.g., a first intermediate probe such as a first L-probe), the second probe (e.g., a second intermediate probe such as a second L-probe), and one or more subsequent probes (e.g., subsequent intermediate probe such as subsequent L-probes) are contacted with the biological sample sequentially in a predetermined sequence which corresponds to the signal code sequence assigned to the identifier sequence (e.g., barcode sequence or analyte sequence), wherein the one or more subsequent probes each comprises (i) a recognition sequence complementary to the identifier sequence (e.g., barcode sequence or analyte sequence) and (ii) an overhang sequence complementary to a detectably labeled probe of a pool (e.g., a universal pool across different cycles of probe hybridization) of detectably labeled probes. In some embodiments, the biological sample is contacted with the first probe before the second probe and one or more subsequent probes. In some embodiments, the biological sample is contacted with the second after the first probe and before and one or more subsequent probes. In some embodiments, the biological sample is contacted with the one or more subsequent probes after the first probe. In some embodiments, the biological sample is contacted with the one or more subsequent probes after the first probe and the second probe.

In some embodiments, the first detectably labeled probe and the second detectably labeled probe are in the pool of detectably labeled probes. A pool of detectably labeled probes may comprises at least two detectably labeled probes, and may be used for multiplexing analyses of two or more target analytes (e.g., target nucleic acids) in a biological sample. In some embodiments, the contacting in b)

comprises contacting the biological sample with the universal pool of detectably labeled probes, and the contacting in d) comprises contacting the biological sample with the universal pool of detectably labeled probes. In some embodiments, the universal pool of detectably labeled probes used in the contacting in b) is the same as the universal pool of detectably labeled probes used in the contacting in d). In some embodiments, the universal pool comprises detectably labeled probes each having a detectable label corresponding to a different nucleic acid sequence for hybridization to a landing sequence (e.g., an overhang sequence) in a probe (e.g., an intermediate probe such as an L-probe). In some embodiments, the number of different detectably labeled probes in the universal pool is four.

In some embodiments, the one or more subsequent probes are contacted with the biological sample to determine signal codes in the signal code sequence until sufficient signal codes have been determined to decode the identifier sequence (e.g., barcode sequence or analyte sequence), thereby identifying the target analyte (e.g., target nucleic acid). In some embodiments, the method further comprises a step of removing the first probe and/or the first detectably labeled probe from the biological sample before contacting the sample with a subsequent probe and a detectably labeled probe hybridizing to the subsequent probe. In some embodiments, the method further comprises a step of removing the second probe and/or the second detectably labeled probe from the biological sample, before contacting the sample with a subsequent probe and a detectably labeled probe hybridizing to the subsequent probe.

In some embodiments, the method further comprises identifying multiple different target analytes present at locations (e.g., different locations) in the biological sample. In some embodiments, each different target analyte is assigned a different signal code sequence and is targeted by a circular or circularizable probe or probe set (e.g., a self-compacting circularizable probe or probe set described in Section III) comprising a complement of a different barcode sequence of the plurality of barcode sequences. In some embodiments, the number of different probes (e.g., L-probes that have different recognition sequences that bind to the barcode sequences) in each pool of probes is greater than the number of different detectably labeled probes in the universal pool of detectably labeled probes. In some embodiments, the number of different detectably labeled probes in the universal pool is four. In some embodiments, the number of different probes in each pool of probes (e.g., L-probes) is about 10, about 20, about 30, about 40, about 50, about 100, about 200, about 500, about 1,000, or more. In some embodiments, the number of different recognition sequences (e.g., recognition sequences that bind to the barcode sequences) of probes in each pool of probes in at least about 10, such as at least any of about 20, 30, 40, 50, 100, 200, 500, 1,000, or more.

In some embodiments, sequence detection can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. *Science* (2005), 309: 1728-1732, and in U.S. Pat. Nos. 5,599,675; 5,750,341; 6,969,488; 6,172,218; and 6,306,597.

In some embodiments, the barcodes of the detection probes are targeted by detectably labeled secondary probe oligonucleotides, such as fluorescently labeled oligonucleotides. In some embodiments, one or more decoding schemes are used to decode the signals, such as fluorescence, for sequence determination. In any of the embodiments herein, barcodes (e.g., barcode sequences of circular or circularizable probes or probe sets) can be analyzed (e.g., detected or sequenced) using any suitable methods or techniques, comprising those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labelled probes (e.g., detection oligonucleotides). Exemplary decoding schemes are described in Eng et al., "Transcriptome-scale Super-Resolved Imaging in Tissues by RNA SeqFISH+," *Nature* 568(7751):235-239 (2019); Chen et al., "Spatially resolved, highly multiplexed RNA profiling in single cells," *Science;* 348(6233):aaa6090 (2015); Gyllborg et al., Nucleic Acids Res (2020) 48(19): e112; U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004).

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and Korlach et al., *Proc. Natl. Acad. Sci. USA* (2008), 105, 1176-1181.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

VI. Compositions, Kits, and Systems

In some embodiments, disclosed herein is a composition that comprises a circular probe or circularizable probe or probe set capable of hybridizing to a sequence of a target nucleic acid in the biological sample (e.g., as described in Section III). In some embodiments, the circular probe or circularizable probe or probe set comprises one, 2, 3, 4, 5, 6, or more stem-loop structures. In some embodiments, the composition comprises a circular or circularizable probe or probe set wherein a loop region of a stem-loop structure comprises a sequence that hybridizes to the target nucleic acid. In some embodiments, the composition comprises a circularizable probe or probe set, wherein a loop region of the stem-loop structure comprises a primer binding sequence for initiating rolling circle amplification. In some embodiments, the composition comprises a circularizable probe comprising four stem-loop structures and a double-stranded central region. In certain embodiments, the circularizable probe comprises two or more nucleic acid molecules that are ligated together to form a circularized probe.

Also provided herein are kits, for example, comprising any of the circular probes or circularizable probes or probe sets described herein (e.g., as described in Section III), and instructions for performing the methods provided herein. In some embodiments, the kits further comprise one or more reagents required for one or more steps comprising hybridization, ligation, extension, detection, sequencing, and/or sample preparation as described herein. In some embodiments, the kit further comprises a target nucleic acid, e.g., any described in Sections II. In some embodiments, any or all of the circular probes or circularizable probes or probe sets are DNA molecules. In some embodiments, the target nucleic acid is a messenger RNA molecule. In some embodiments, the target nucleic acid is a probe or an amplification or extension product thereof. In some embodiments, the target nucleic acid is comprised by a labelling agent (e.g., an antibody conjugated to a reporter oligonucleotide). The various components of the kit may be present in separate containers or certain compatible components may be pre-combined into a single container. In some embodiments, the kits further contain instructions for using the components of the kit to practice the provided methods.

In some embodiments, provided herein is a kit comprising a circular or circularizable probe or probe set wherein the circular probe or circularizable probe or probe set comprises a first stem-loop structure, a second stem-loop structure, a third stem-loop structure, a fourth stem-loop structure, and a double stranded central structure which is between the stem regions of adjacent stem-loop structures and is non-overlapping with the stem regions. In some embodiments, the circular or circularizable probe or probe set is capable of hybridizing to a target nucleic acid in a biological sample. In some embodiments, each stem-loop structure comprises, from 5' to 3' a first stem sequence, a loop sequence, and a second stem sequence, wherein the second stem sequence comprises a reverse complement sequence of the first stem sequence. In some embodiments, the loop regions of the first, second, third, and/or fourth stem-loop structures independently comprise (i) a 5' end sequence and a 3' end sequence complementary to the target nucleic acid and/or (ii) one or more barcode sequences. In some embodiments, the circularizable probe or probe set is capable of being circularized by ligating the 5' end sequence and the 3' end sequence hybridized to the target nucleic acid. In some embodiments, the circularizable probe comprises two or more nucleic acid molecules that are ligated together to form a circularized probe.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as barcode detection probes or detectable labels. In some embodiments, the kits optionally contain other components, for example nucleic acid primers, enzymes and reagents, buffers, nucleotides, and reagents for additional assays.

VII. Applications

In some aspects, the provided embodiments can be applied in an in situ method of analyzing nucleic acid sequences, such as an in situ transcriptomic analysis or in situ sequencing, for example from intact tissues or samples in which the spatial information has been preserved. In some aspects, the embodiments can be applied in an imaging or detection method for multiplexed nucleic acid analysis. In some aspects, the provided embodiments can be used to generate compacted rolling circle amplification products, e.g., to increase the resolution and stability of the rolling circle amplification products in situ.

In some aspects, the embodiments can be applied in investigative and/or diagnostic applications, for example, for characterization or assessment of particular cell or a tissue from a subject. Applications of the provided method can comprise biomedical research and clinical diagnostics. For example, in biomedical research, applications comprise, but are not limited to, spatially resolved gene expression analysis for biological investigation or drug screening. In clinical diagnostics, applications comprise, but are not limited to, detecting gene markers such as disease, immune responses, bacterial or viral DNA/RNA for patient samples.

In some aspects, the embodiments can be applied to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, or in personalized medicine or ancestry.

VIII. Terminology

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms "polynucleotide," "polynucleotide," and "nucleic acid molecule", used interchangeably herein, refer to polymeric forms of nucleotides of any length, either ribonucleotides or deoxyribonucleotides. Thus, this term comprises, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers. Hybridization temperatures can be as low as 5° C., but are typically greater than 22° C., and more typically greater than about 30° C., and typically in excess of 37° C. Hybridizations are often performed under stringent conditions, i.e., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985)). Other references (e.g., Allawi and SantaLucia, Jr., Biochemistry, 36:10581-94 (1997)) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, "stringency of hybridization" in determining percentage mismatch can be as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, Nucleic Acids Res. 12:203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Sequencing," "sequence determination" and the like means determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput digital sequencing" or "next generation sequencing" means sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technologies, Inc., Carlsbad, Calif.); sequencing by synthesis using modified nucleotides (such as commercialized in TruSeq™ and HiSeq™ technology by Illumina, Inc., San Diego, Calif.; HeliScope™ by Helicos Biosciences Corporation, Cambridge, Ma.; and PacBio RS by Pacific Biosciences of California, Inc., Menlo Park, Calif.), sequencing by ion detection technologies (such as Ion Torrent™ technology, Life Technologies, Carlsbad, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

"Multiplexing" or "multiplex assay" herein may refer to an assay or other analytical method in which the presence and/or amount of multiple targets, e.g., multiple nucleic acid target sequences, can be assayed simultaneously by using more than one probe conjugate, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

The term "about" as used herein refers to the usual error range for the respective value readily known to the skilled person in this technical field. Reference to "about" a value or parameter herein comprises (and describes) embodiments that are directed to that value or parameter per se.

As used herein, the singular forms "a," "an," and "the" comprise plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be comprised in the smaller ranges, and are also encompassed within the claimed subject matter, subject to any specifically excluded limit in the stated range. Where the stated range comprises one or both of the limits, ranges excluding either or both of those comprised limits are also comprised in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

EXAMPLES

The following examples are included for illustrative purposes only and are not intended to limit the scope of the present disclosure.

Example 1: Generating a Self-Compacting Rolling Circle Amplification Product

This example demonstrates a method for analyzing a biological sample comprising hybridizing a circular or circularizable probe or probe set disclosed herein to a sequence of a target nucleic acid in the biological sample and generating an amplification product using the circular probe or a circularized probe generated from the circularizable probe or probe set as a template. The circular or circularizable probe or probe set comprises a first stem-loop structure, a second stem-loop structure, a third stem-loop structure, and a fourth stem-loop structure, as shown in FIG. 1A. The circular or circularizable probe or probe set can comprise a double stranded central structure as shown in FIG. 1A. The amplification product generated from the circular probe or circularized probe comprises multiple copies of a unit structure comprising sequences complementary to the first stem-loop structure, second stem-loop structure, third stem-loop structure, and fourth stem-loop structure, and double stranded central structure. In some aspects, formation of the unit structures in the amplification product and/or steric hindrance between unit structures promotes compaction of the amplification product.

A biological sample (e.g., a processed or cleared biological sample, a tissue sample, a sample embedded in a hydrogel, or a fixed and paraffin embedded sample, etc.) is contacted with a circularizable probe or probe set as described above. The circularizable probe or probe set is hybridized to a target nucleic acid sequence, such as an mRNA or cDNA, in the tissue sample and is ligated to generate a closed circle (e.g., a closed unit structure) from the circularizable probe or probe set. In one example, a circularized probe is generated by a single ligation of a circularized probe, as shown in FIG. 1A (e.g., using the target nucleic acid as a template). In another example, a circularized probe is generated by a first and a second ligation of a circularizable probe set, as shown in FIG. 1B (e.g., using a first sequence and a second sequence of one or more target nucleic acids as templates for ligation). In some cases, the sample can be washed to remove unbound probes before being incubated with a ligase for ligation.

For amplification, a primer that hybridizes to a sequence of one of the loops of the stem-loop structure may be added to the sample. The circular or circularized probe is then amplified by a DNA polymerase in a RCA reaction to generate a rolling circle amplification product (RCP) comprising multiple copies of a sequence complementary to the circular or circularizable probe or probe set. In an example, the sequences complementary to the circular or circularizable probe or probe set form multiple copies of the unit structure (e.g., a structure comprising multiple hairpins, optionally wherein the structure comprises a double stranded central structure as shown in FIGS. 1A-1B).

In an example, the shape of the unit structure (e.g., the stem-loop structures and the double stranded central structure) promote radial expansion (e.g., generation of multiple copies of the unit structure around a central vertex) and/or stacking of unit structures, as shown in FIG. 3. The radial expansion and/or stacking of unit structures facilitates compaction of the RCP. For example, the formation and/or packing of unit structures in the RCP can facilitate self-compaction of the RCP (e.g., without requiring the use of additional oligonucleotides that hybridize to the RCP and promote compaction).

Detection of sequences of the RCA product can be performed using sequencing by synthesis (SBS), sequencing by ligation (SBL), or sequencing by hybridization (SBH). For example, fluorescently labeled oligonucleotides complementary to a portion of the RCA product, a barcode contained therein, or a secondary probe attached thereto are incubated with the sample. For example, one or more of the loop regions of the stem-loop structures may include a barcode sequence associated with the target nucleic acid. Multiple cycles of contacting the sample with probes and sequence determination (e.g., using in situ sequencing based on sequencing-by-ligation or sequencing-by-hybridization) can be performed. Fluorescent images can be obtained in each cycle, and one or more wash steps can be performed in a cycle or between cycles. Probes targeting target nucleic acids can be sequentially or simultaneously provided, processed, and detected as described above.

Example 2: Detection of Prox1 RNA Using Rolling Circle Amplification of a Self-Compacting Circularizable Probe This example demonstrates a method for analyzing a biological sample comprising hybridizing a circular or circularizable probe or probe set disclosed herein to a sequence of a target nucleic acid (Prox1 RNA).

A fresh frozen mouse brain tissue sample was contacted with a control circularizable padlock probe (with no stem loop sequences) or a self-compacting circularizable probe comprising a first stem-loop structure, a second stem-loop structure, a third stem-loop structure, a fourth stem-loop structure, and a double stranded central structure as shown in FIG. 1A. Three self-compacting circularizable probes tested ("self-compacting circularizable probe," "self-compacting circularizable probe—anchor," "self-compacting circularizable probe—2 barcodes") each shared the same backbone sequences and a first step-loop structure (e.g., formed by the 5' end sequence and the 3' end sequence of the probe polynucleotide) that hybridized to complementary sequences in the Prox1 RNA. The "self-compacting circularizable probe—anchor" was modified in the anchor/primer binding sequence to be less prone to additional secondary structure and a larger third stem-loop structure. The "self-compacting circularizable probe—2 barcodes" had the modified anchor/primer binding sequence and additionally was modified in the fourth stem-loop structure with an additional barcode sequence.

The circularizable padlock probe or self-compacting circularizable probe were added to the sample and allowed to hybridize. Samples were washed to remove unbound probes. For ligation, a ligase in a ligation reaction mix was added to the sample to circularize the probes. For amplification, a primer that hybridizes to a sequence of one of the loops of the stem-loop structure was added to the sample. The circular or circularized probe was then amplified by incubating the samples with a reaction mix containing Phi29 polymerase buffer, dNTPs, and Phi29 polymerase to generate a rolling circle amplification product (RCP).

Detection of sequences of the RCA product was performed by hybridizing fluorescently labeled oligonucleotides complementary to a portion of the RCA product (e.g., barcode in one or more of the loop regions of the stem-loop structures associated with the target nucleic acid) and imaged with a fluorescent microscope.

Figure 5:
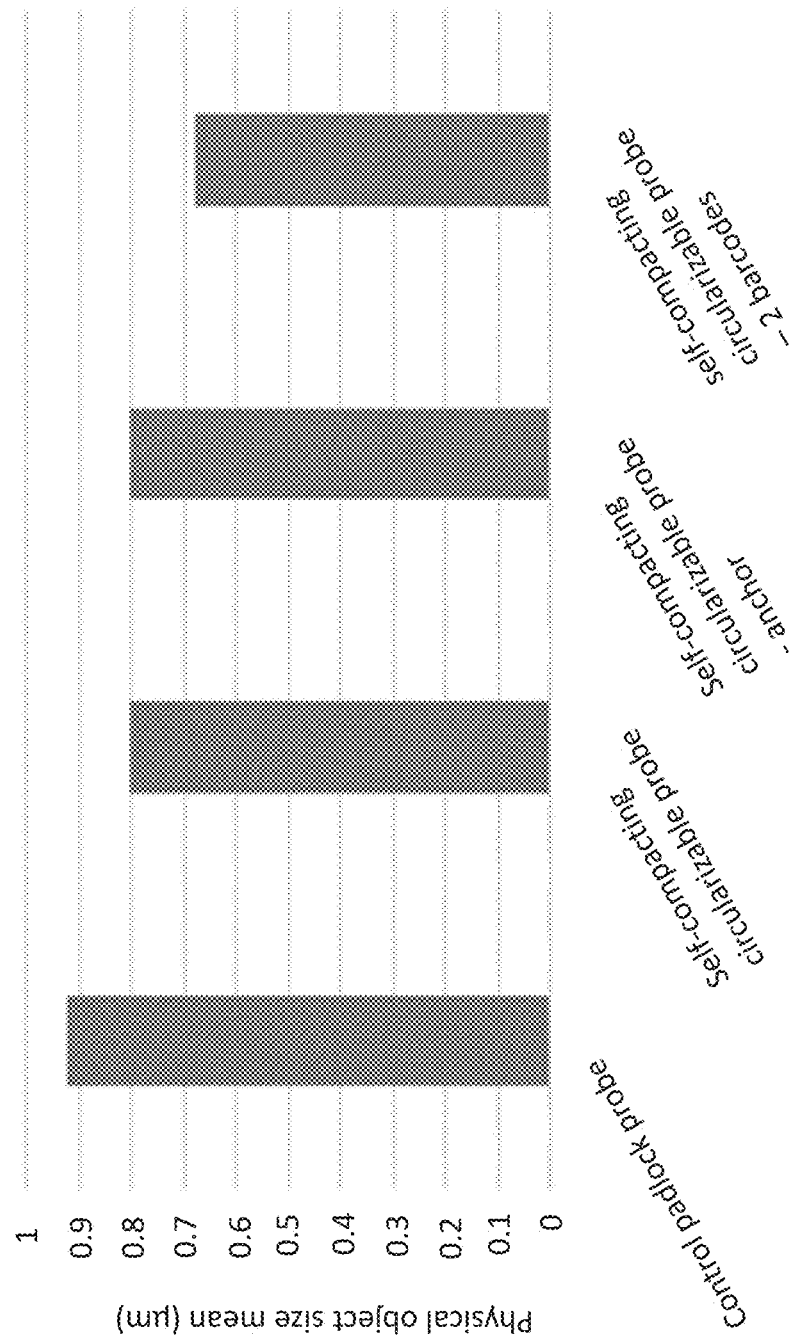
FIG. 5 shows the physical object size of detected amplification products generated using control circularizable padlock probes and exemplary self-compacting circularizable probes comprising a first stem-loop structure, a second stem-loop structure, a third stem-loop structure, a fourth stem-loop structure, and a double stranded central structure.

FIG. 5 shows physical object size detected of each of the circularizable probes tested. Compared to the control circularizable padlock probe (with no stem loop sequences), self-compacting circularizable probes generated amplification products of smaller sizes. In particular, the self-compacting circularizable probe with the modified anchor/primer binding sequence and 2 barcode sequences ("self-compacting circularizable probe—2 barcodes") showed approximately 32% decrease in object size compared to the control circularizable padlock probe.

The present disclosure is not intended to be limited in scope to the particular disclosed embodiments, which are provided, for example, to illustrate various aspects of the disclosure. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for analyzing a biological sample, comprising:
   (a) hybridizing a circularizable probe or a circularizable probe set to a sequence of a target nucleic acid in the biological sample and ligating the circularizable probe or the circularizable probe set to generate a circularized probe using the target nucleic acid as a template,
   wherein the circularized probe comprises a four-hairpin base unit structure comprising a first stem-loop structure, a second stem-loop structure, a third stem-loop structure, and a fourth stem-loop structure, wherein each stem-loop structure independently comprises, from 5' to 3', a first stem sequence, a loop region, and a second stem sequence comprising a reverse complement of the first stem sequence,
   wherein each stem region of the first stem-loop structure, the second stem-loop structure, the third stem-loop structure, and the fourth stem-loop structure comprises a different sequence,
   wherein the loop region of the first stem-loop structure comprises a sequence complementary to the target nucleic acid that is used as the template to generate the circularized probe;
   (b) generating a rolling circle-amplification (RCA) product using the circularized probe as a template,
   wherein the rolling circle amplification product comprises multiple complementary copies of the four-hairpin base unit structure comprising complementary sequences of the first stem-loop structure, the second stem-loop structure, the third stem-loop structure, and the fourth stem-loop structure; and
   (c) detecting the RCA product in the biological sample or in a matrix embedding the biological sample or molecules thereof.

2. The method of claim 1, wherein the circularized probe comprises a double stranded central structure between the stem regions of the first and second stem-loop structures.

3. The method of claim 2, wherein a first strand of the double stranded central structure is between the stem regions of the first and second stem-loop structures and a second strand of the double stranded central structure is between the stem regions of the third and fourth stem-loop structures.

4. The method of claim 1, wherein detecting the rolling circle amplification product comprises contacting the biological sample with one or more detectably-labeled probes that directly or indirectly bind to one or more loop regions of the rolling circle amplification product.

5. The method of claim 1, wherein a signal associated with the rolling circle amplification product is amplified in situ in the biological sample or in a matrix embedding the biological sample or molecules thereof.

6. The method of claim 1, wherein the loop regions of the second, third, and/or fourth stem-loop structure independently comprise one or more barcode sequences or complements thereof.

7. The method of claim 1, wherein the loop region of the second, third, or fourth stem-loop structure comprises a primer binding sequence for initiating rolling circle amplification.

8. The method of claim 2, wherein the double stranded central structure is between the stem regions of adjacent stem-loop structures.

9. The method of claim 1, wherein the four-hairpin base unit structure comprises stem-loop and double stranded central structures that facilitate generation of a multi-unit structure comprising multiple complementary copies of the four-hairpin base unit structure around a central vertex, and wherein the multi-unit structure comprises 3, 4, or 5 complementary copies of the four-hairpin base unit structure around the central vertex.

10. A method for analyzing a biological sample, comprising:
   (a) contacting a biological sample with a circularizable probe that hybridizes to a target nucleic acid in the biological sample, and generating a circularized probe from the circularizable probe by ligating the 5' end sequence and the 3' end sequence hybridized to the target nucleic acid,
   wherein the circularized probe comprises a four-hairpin base unit structure comprising:
      a first stem-loop structure,
      a second stem-loop structure,
      a third stem-loop structure,
      a fourth stem-loop structure, and
      a double stranded central structure that is between the stem regions of adjacent stem-loop structures, and
   wherein each stem-loop structure independently comprises, from 5' to 3' a first stem sequence, a loop region, and a second stem sequence comprising a reverse complement of the first stem sequence;
   wherein each stem region of the first stem-loop structure, the second stem-loop structure, the third stem-loop structure, and the fourth stem-loop structure comprises a different sequence,
   wherein the loop region of the first stem-loop structure comprises a sequence complementary to the target nucleic acid that is used as the template to generate the circularized probe;
   wherein the loop regions of the second, third, and/or fourth stem-loop structures independently comprise (i) a sequence complementary to the target nucleic acid and/or (ii) one or more barcode sequences;
   (b) generating a rolling circle amplification (RCA) product using the circularized probe as a template, wherein the RCA product comprises multiple copies complementary copies of the four-hairpin base unit structure comprising complementary sequences of the first, second, third, and fourth stem-loop structures and the double stranded central structure; and
   (c) detecting the RCA product in situ in the biological sample or in a matrix embedding the biological sample or molecules thereof.

* * * * *

SEQUENCE LISTING

```
Sequence total quantity: 1
SEQ ID NO: 1          moltype = DNA  length = 200
FEATURE               Location/Qualifiers
source                1..200
                      mol_type = other DNA
                      organism = synthetic construct
misc_feature          200
                      note = RNA
misc_feature          1..199
                      note = DNA
SEQUENCE: 1
taactccgtg gaccactgca gcccaagggc atgagatacg acccactggc aggtaataag    60
gtgcccttga gcaagagcct gcctgagaca tacgacccac tggcaggtaa gcagccaggc   120
aggagtcggg gagacatacg acccactggc aggtaagcag ccccgactc tcttgctggc   180
tgcaggatac ggaacaacac                                               200
```